(12) United States Patent
Tian et al.

(10) Patent No.: US 10,130,945 B2
(45) Date of Patent: Nov. 20, 2018

(54) CELL PATHOLOGY TUBES AND ASSOCIATED CELL PROCESSING METHODS

(71) Applicant: Wake Forest University Health Sciences, Winston-Salem, NC (US)

(72) Inventors: Shaozhou Ken Tian, Clemmons, NC (US); Kim R. Geisinger, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/373,548

(22) Filed: Dec. 9, 2016

(65) Prior Publication Data

US 2017/0087548 A1    Mar. 30, 2017

Related U.S. Application Data

(62) Division of application No. 14/410,707, filed as application No. PCT/US2013/047619 on Jun. 25, 2013, now Pat. No. 9,557,251.

(60) Provisional application No. 61/664,985, filed on Jun. 27, 2012.

(51) Int. Cl.
| | |
|---|---|
| *G01N 1/10* | (2006.01) |
| *B01L 3/00* | (2006.01) |
| *C12Q 1/24* | (2006.01) |
| *G01N 1/36* | (2006.01) |

(52) U.S. Cl.
CPC ........... *B01L 3/5021* (2013.01); *C12Q 1/24* (2013.01); *G01N 1/36* (2013.01); *B01L 2300/042* (2013.01); *B01L 2300/047* (2013.01); *B01L 2300/0851* (2013.01); *B01L 2300/0858* (2013.01)

(58) Field of Classification Search
CPC ....................................................... G01N 1/00
See application file for complete search history.

(56) References Cited

U.S. PATENT DOCUMENTS

| | | |
|---|---|---|
| 5,137,710 A | 8/1992 | Smalley et al. |
| 5,234,667 A | 8/1993 | Li et al. |
| 5,301,685 A | 4/1994 | Guirguis |
| 6,913,921 B2 | 7/2005 | Fischer |
| 8,322,539 B1 | 12/2012 | Ellis et al. |
| 2002/0110923 A1 | 8/2002 | Robinson |
| 2005/0101879 A1 | 5/2005 | Shidham |

(Continued)

FOREIGN PATENT DOCUMENTS

| | | |
|---|---|---|
| WO | WO 1995/027561 A1 | 10/1995 |
| WO | WO 2010/014970 A1 | 2/2010 |

OTHER PUBLICATIONS

Hecht et al. "Comparison of three cell block techniques for detection of low frequency abnormal cells" *Pathology and Laboratory Medicine International* 5:1-7 (2013).

(Continued)

*Primary Examiner* — Jyoti Nagpaul
(74) *Attorney, Agent, or Firm* — Myers Bigel, P.A.

(57) ABSTRACT

Cell tubes that can be used both for pathology collection and subsequent cell processing include a tube with a cell bed at a lower portion of the tube. The tube can include a base member that can be detachable from the tube body. The tubes can be used to form cell (cytology) blocks that incorporate the cell bed. The cell bed can be an inert cell bed of paraffin.

20 Claims, 24 Drawing Sheets

(56) References Cited

U.S. PATENT DOCUMENTS

| | | |
|---|---|---|
| 2007/0111194 A1 | 5/2007 | Pellaux et al. |
| 2007/0218542 A1* | 9/2007 | Li .......................... C12M 23/42 435/283.1 |
| 2008/0068707 A1 | 3/2008 | Goodman |
| 2010/0216220 A1 | 8/2010 | Dawson |
| 2011/0250586 A1 | 10/2011 | Halverson |

OTHER PUBLICATIONS

International Preliminary Report on Patentability corresponding to International Patent Application No. PCT/US2013/047619 (11 Pages) (dated Jan. 8, 2015).

International Search Report and the Written Opinion of the International Searching Authority corresponding to International Patent Application No. PCT/US2013/047619 (16 pages) (dated Sep. 25, 2013).

Nathan et al. "Improved Preparation and Its Efficacy in Diagnosing Cytology" *American Journal of Clinical Pathology* 114:599-606 (2000).

Thermo Electron Corporation, Shandon Cytoblock® Cell Block Preparation System, Rev. 4, Date stated as Sep. 2003, which is believed to be either Sep. 2003 or Mar. 2009, 6 Pages.

\* cited by examiner

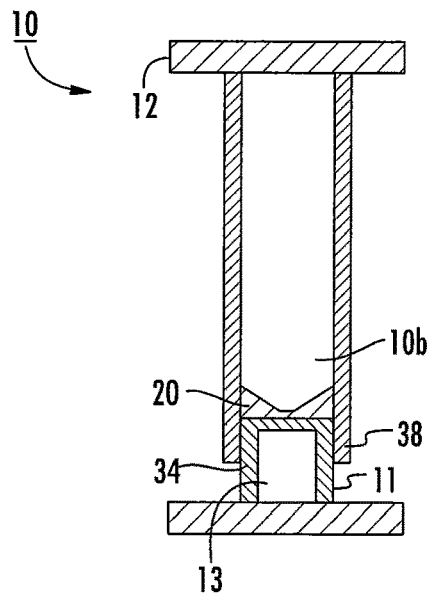
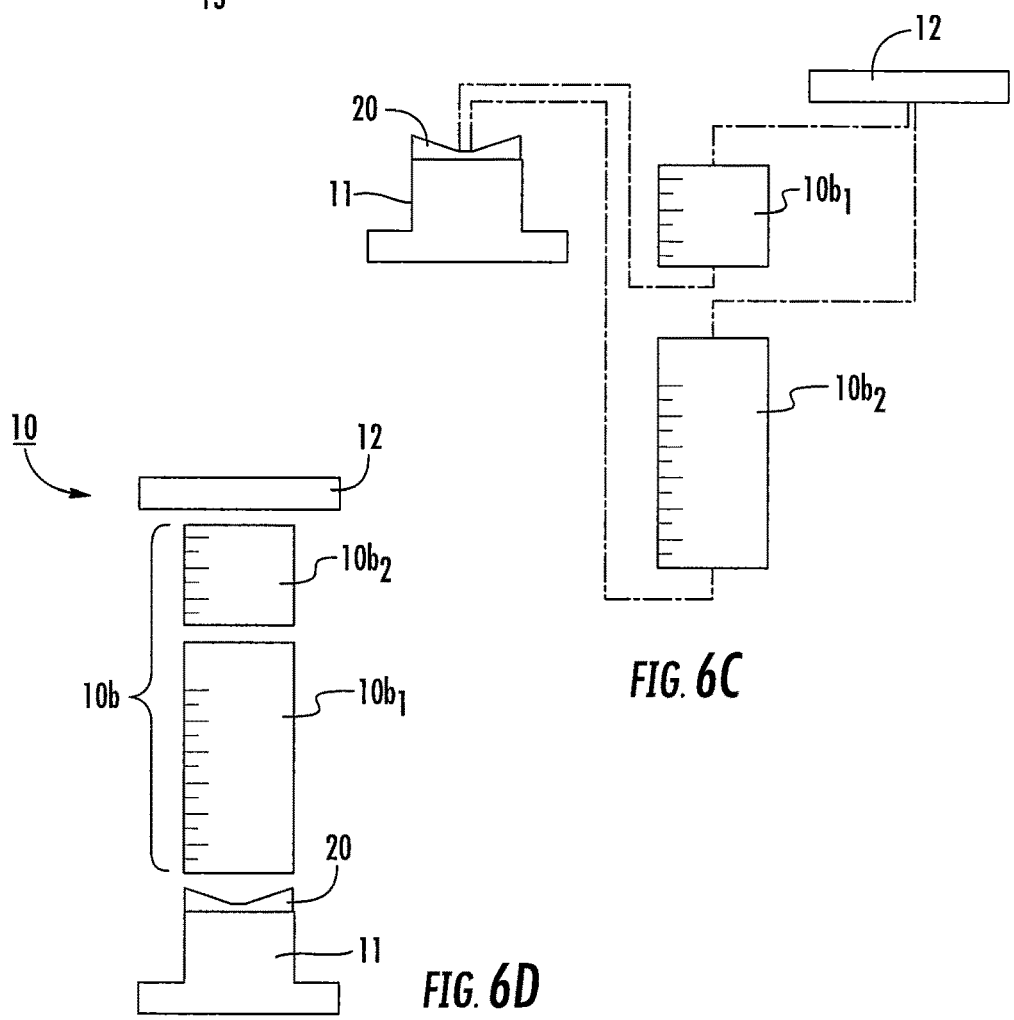
FIG. 6B
FIG. 6C
FIG. 6D

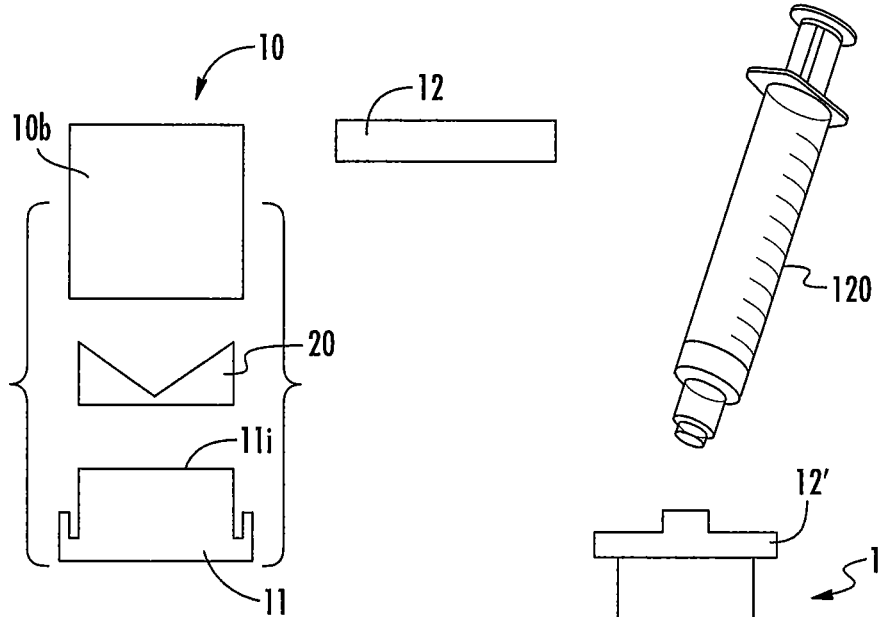
FIG. 11
FIG. 12
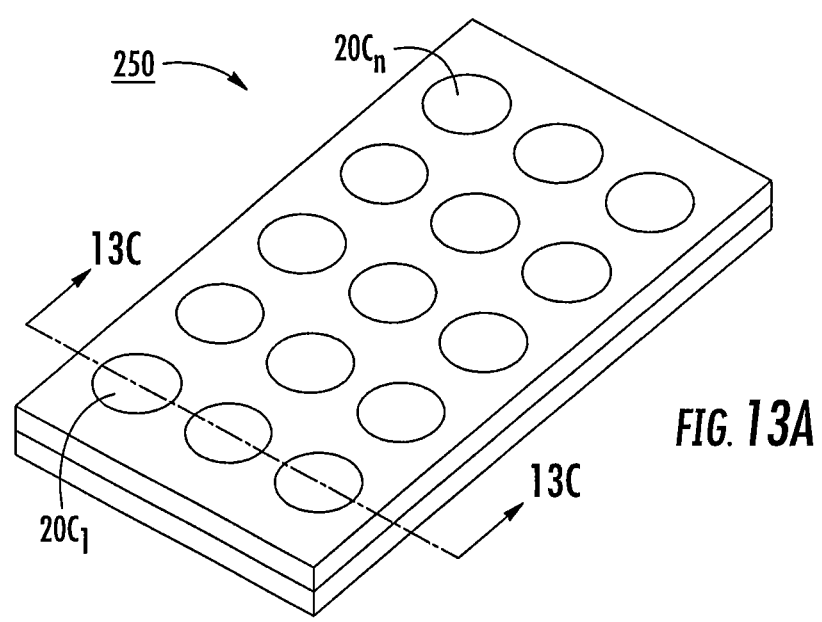
FIG. 13A

CELL PATHOLOGY TUBES AND ASSOCIATED CELL PROCESSING METHODS

RELATED APPLICATIONS

This application is a divisional of U.S. application Ser. No. 14/410,707, filed Dec. 23, 2014, which is a 35 U.S.C. 371 National Phase Application of PCT/US2013/047619, filed Jun. 25, 2013, which claims priority to and the benefit of U.S. Provisional Application Ser. No. 61/664,985, filed Jun. 27, 2012, the contents of each of which are hereby incorporated by reference as if recited in full herein.

FIELD OF THE INVENTION

This invention relates to cell pathology tubes for cell collection and/or processing.

BACKGROUND OF THE INVENTION

Compared to core or open biopsies, fine needle aspirates (FNA) are a quick and relatively safe method of biopsy to provide samples for evaluation of clinically suspicious mass lesions. FNA are often a first step in evaluating whether a patient has a malignancy. Routine collections during FNA include paired smears (Diff-Quick and H&E) and cell block (clot block or cell disk). Each collection is from a single pass or aspiration. The paired smears are routinely performed on most of the passes to rapidly evaluate the morphology of the suspicious lesion. The cell block is used to process the specimen in a manner to allow for ancillary testing. For example, the cell block can be used to evaluate immunohistochemistry, FISH, PCR and the like, as well as to assess morphology. The morphology of blocks may be diagnostically complimentary in that they often provide more data with regard to the architectural arrangement of cells compared to smears. The evaluation of cells from FNAs typically employs very limited cell material. It is a known problem that the quality of the cell block can deteriorate compared to paired cell smears from the same procedure. Unfortunately, this deterioration can impair additional, sometimes confirmatory, testing or analysis that can be carried out on the specimen. This can result in an inconclusive diagnosis typically requiring additional diagnostic procedures at increased risk and/or cost to the patient and may delay specific therapy.

In the past, the cell blocks have been prepared using samples that are expelled onto glass slides and placed in formalin within a short time frame. The cell block is allowed to "clot" together to make a relatively solid specimen that can be processed to make formalin-fixed paraffin embedded (FFPE) tissue samples. This cell block preparation process can result in undue cell loss resulting in decreasing (and sometimes no) cell yields in the FFPE tissue samples.

SUMMARY OF EMBODIMENTS OF THE INVENTION

Embodiments of the invention provide tubular devices with integrated cell beds (e.g., paraffin beds) that can directly receive cells from a FNA or other sources at a collection site without requiring the use of a glass slide.

Embodiments of the invention provide tubular devices that can be used for the collection, transfer and subsequent centrifuge processing of tissue samples to form a cell block with suspended cells.

Aspects of the invention are directed to methods of collecting and processing a biosample. The methods include: (a) providing a tubular container with an internal cavity having a cell bed residing above a closed bottom end of the container; (b) inserting a biosample comprising cells into the tubular container so that cells reside on the cell bed; (c) placing the tubular container with the cell bed and biosample in a centrifuge; (d) centrifuging the biosample in the tubular container so that cells from the biosample deposit as a pellet against the cell bed; (e) inserting a liquid matrix material in the tubular container above the cell bed; (f) forming a solid cell block of the liquid matrix material holding distributed cells therein above the cell bed; and (g) removing the solid cell block with the cell bed from the tubular container.

The cell bed can be a solid, shape-changeable, moldable material that is able to change in shape in response to forces above those applied during the centrifuging step and can retain that shape during the inserting, centrifuging, forming and removing steps.

The cell bed can include solid paraffin and extends across the tubular container.

The cell bed can have a middle portion with a substantially conical shape that merges into an outer cylindrical upwardly extending outer portion that conformably attaches to an inner surface of a sidewall of the tube and the cell bed defines a closed solid cell bed surface.

Inserting the biosample can be carried out by depositing cells from a fine needle aspirate directly from a needle holding the aspirate onto the cell bed.

Placing the tubular container in the centrifuge can optionally be carried out by first placing the tubular container holding the biosample on the cell bed in a coupler, adapter or larger tube forming a centrifuge assembly, then placing the assembly in a bucket of the centrifuge and centrifuging the assembly.

The cell block can include cells from a fine needle aspirate tissue sample. The method can include, before the centrifuging step, inverting the tubular container with the cell bed, then attaching the tubular container to an open end of an elongate body comprising a liquid, then inverting the tubular container with the cell bed while attached to the elongate body with the liquid so that the cell bed is at a lower end of the tubular container, then centrifuging the biosample in the tubular container.

Other embodiments are directed to cell pathology containers. The containers can have a tubular body having an open interior space and open opposing first and second end portions. A base is removably attached to the second end portion of the tubular body. A solid cell bed resides in the tubular body proximate the base.

The cell bed can have a substantially planar bottom.

The cell bed can have a solid, shape-changeable, moldable material that is able to retain a defined conical or frustoconical shape.

The cell bed can include solid paraffin and extend across the tubular container to define a closed cell bed surface.

The cell bed can have a middle portion with a substantially conical shape.

The cell bed can have a middle portion that merges into an outer cylindrical upwardly extending outer portion that conformably attaches to an inner surface of a sidewall of the tube and the cell bed can define a closed solid cell bed surface.

The solid cell bed can be pre-formed in the tubular body and/or base and can define a closed solid cell bed surface, and wherein the container is enclosed in sterile packaging.

The base can include an internal substantially planar surface that holds the cell bed.

The base can hold a spacer that rises above a lower portion of the base and extends into the tubular body, and the spacer can include an upper substantially planar surface that holds the cell bed.

The base can include an annular recess that surrounds the planar surface and engages a lower portion of the tubular body.

The tubular body first portion can releasably attach to either or both of a cap or elongate body having a length that is greater than that of the tubular body.

The base and cap can have respective ledges of substantially common diameter that extend radially outward from a centerline of the container to reside a distance beyond a diameter of the tubular body.

The container can have a volume that is between about 10 mL to about 100 mL. The tubular body has threads on upper and lower portions thereof, the lower portion configured to threadably attach to the base.

The tubular body can be sterile and configured to hold human or animal cell samples.

The first end portion of the tubular body can be attached to an open end of the elongate body. The elongate body can have a tapered segment that merges into a lower segment having a greater outer diameter. The elongate body can have a removable end cap on an end opposing the open end.

Embodiments of the invention provide cell disks that can be used to make pathology or diagnostic specimens, e.g., surgical pathology FFPE specimens from any kind of cellular source, e.g., suspension. This applies to body fluids (pleural, pericardial, lung washing, etc.). These fluids have diagnostic utility, but also might be the only specimen in certain cases.

Special stains for amyloid or microorganisms can also be performed on any collected specimen, e.g., any FFPE specimens. This can be adapted to fluids for diagnosis.

Other aspects are directed to methods of collecting a biosample. The methods include: (a) providing a tubular container with an internal cavity having a pre-formed solid paraffin cell bed residing above a closed bottom end of the container; (b) inserting a needle with a fine needle aspirate sample comprising cells into the tubular container so that cells reside on the cell bed; and either (c)(i) placing a cap on the container before or after inserting the biosample or (c)(ii) attaching the tubular container with the cell bed on an upper portion of an elongate body with liquid and cells from other passes of FNA.

Yet other methods are directed to methods of processing a biosample. The methods include: (a) obtaining a tubular container with an internal cavity having a solid cell bed residing above a closed bottom end of the container and a biosample comprising cells that reside on the cell bed, wherein the tubular container with the solid cell bed and biosample is obtained from a collection site; (b) centrifuging the biosample in the obtained tubular container so that cells from the biosample deposit as a pellet against the cell bed; (c) inserting a liquid matrix material in the tubular container above the cell bed; (d) forming a solid cell block of the liquid matrix material holding distributed cells therein above the cell bed; and (e) removing the solid cell block with the cell bed from the tubular container.

Still other aspects of the invention are directed to methods of making cell beds for cell pathology containers. The methods include forming solid paraffin into a defined cell bed shape so that the cell bed has a middle portion with a substantially conical or frustoconical shape that merges into an outer cylindrical upwardly extending outer portion that conformably attaches to an inner surface of a sidewall of the tube and the cell bed defines a closed solid cell bed surface.

The tubular container holding the biosample on the cell bed can include an elongate body attached to an upper end thereof. The elongate body can include liquid with supplemental cells from needles used to obtain additional fine needle aspirates of target tissue corresponding to the biosample on the cell bed. The centrifuging can be carried out to form a pellet of the biosample cells and the supplemental cells.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 6B is a section view of another example of a container according to embodiments of the present invention.

FIG. 6C is an exploded schematic illustration of an exemplary container with interchangeable tubular bodies according to embodiments of the present invention.

FIG. 6D is an exploded schematic illustration of another exemplary container with stackable container segments according to embodiments of the present invention.

FIG. 11 is a schematic exploded view of a container according to embodiments of the present invention.

FIG. 12 is a schematic illustration of a container with an example of an alternate lid configuration according to embodiments of the present invention.

FIG. 13A is a top perspective view of an exemplary mold for creating formed cell beds according to embodiments of the present invention.

DETAILED DESCRIPTION OF EMBODIMENTS OF THE INVENTION

Figure 1A:
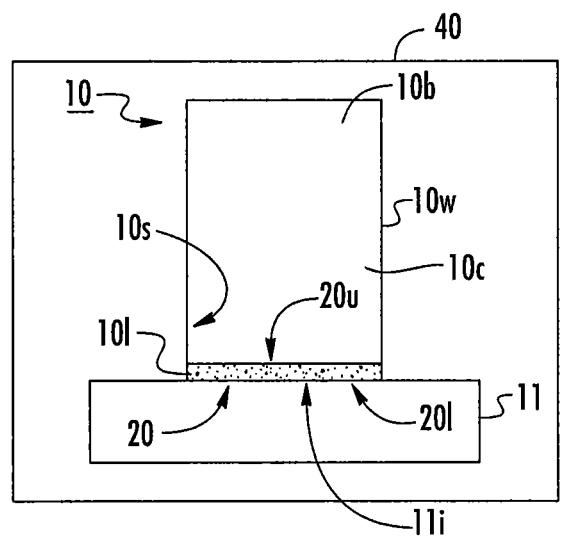
FIG. 1A is a schematic illustration of a biosample container with an integrated cell bed according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

The term "biosample" refers to human or animal tissue, blood or other solid or liquid samples that have cellular material. The cellular material can be limited cellular material, obtained from an FNA or other specimens including, for example, washings, lavages, and endoscopic procedures. Embodiments of the invention can be used for immunohistochemistry (IHC) or other studies including RNA and DNA analysis, research or studies including FISH, PCR and the like and/or to assess morphology. Embodiments of the invention may be used with or for stains, such as "special stains" like Gram stains, Reticulin, Mucin and may others as is well known to those of skill in the art.

Embodiments of the invention provide cell disks that can be used to make surgical pathology FFPE specimens from any kind of suspension. This applies to body fluids (pleural, pericardial, lung washing, etc.). These fluids have diagnostic utility, but also might be the only specimen in certain cases.

Special stains for amyloid or microorganisms can also be performed on any collected specimen, e.g., any FFPE specimens. This can be adapted to fluids for diagnosis.

Embodiments of the invention may be suitable for veterinarian use, medical human use or research for human and/or with laboratory animals.

The term "sterile" means that the noted device or material meets or exceeds defined medical guidelines of cleanliness and is substantially (if not totally) without contaminants so as to be suitable for medical uses (e.g., diagnosis).

Turning now to the figures, FIG. 1A illustrates a cell collection tube 10 with a base 11, an internal cavity 10c and an internal cell bed 20 held proximate the bottom 10l of the tube 10. The cell bed 10 can be an inert cell bed. The term "inert cell bed" refers to a solid material that can support processed cell material above the base 11, typically in a block form, while preserving the cells, typically without chemically interacting with the cells. Post collection and after processing, the cell bed 20 with patient cells C can be removed, substantially intact, e.g., scraped, pushed or otherwise disengaged from the base 11 without disrupting the collected cells thereon for cell evaluation.

Figure 1B:
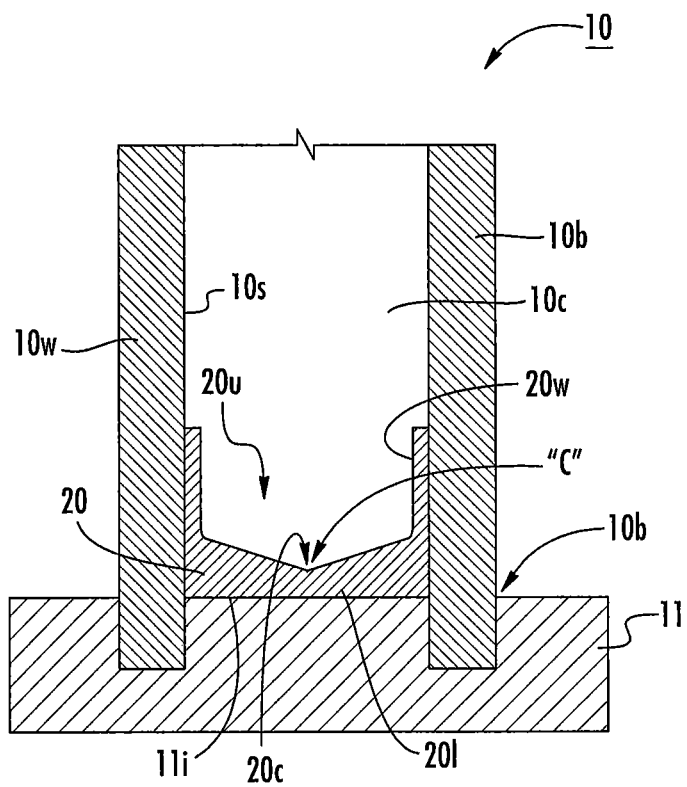
FIG. 1B is a section view of a portion of a biosample container with an example of a shaped cell bed according to embodiments of the present invention.

As shown in FIG. 1A, the cell bed 20 can be substantially planar (e.g., the top and bottom can be flat similar to a flat block). As shown in FIG. 1B, the cell bed 20 can have an upper portion 20u with a defined three-dimensional body shape 20s. The body shape 20s can include a substantially conical or frustoconical center portion 20c for facilitating cell collection during centrifugation. The center portion 20c can taper to have a valley that holds the cells/pellet 100. The cell bed 20 can extend across an entire interior cavity space 10c at the bottom portion of the tube 10l to define a closed surface cell bed above the base 11. In some embodiments, the cell bed 20 can include an upwardly extending outer sidewall 20w that rises a distance above the laterally extending portion and conforms to the inner surface 10i of the tube sidewall 10w at the bottom portion of the tube 10l. The outer perimeter sidewalls 20w can inhibit some samples from being attracted to hydrophilic plastic (polymer) walls of the cylinder 10b that can facilitate forming the cell plug in the desired cell disk or block form. In addition, or alternatively, the taller walls 20w can stay with the cylinder body 10b when separated from the base 11, with the lower portion of the cell bed 20 intact and remaining attached to the walls 20w. In other embodiments, the cell bed walls 20w may detach from the lower cell bed 20 when the base 11 is removed.

In some embodiments, the tube body 10b, base 11 and cap 12 can comprise a molded polymeric material that is sterilized for use. The tube body 10b, base 11 and/or cap 12 may also comprise other suitable materials, including, for example, glass.

In some embodiments, the cell bed 20 has a lower surface 20s that can be substantially planar 20p. The base 11 can also have an internal surface 11i that is substantially planar. However, the base surface 11i can have other shapes and may include narrow channels or slots or can include "waves" or dimples and the like. The surface 11i can be configured to allow for ease of removal of the cell bed 20 with cells in a "cell block" form 100 (FIGS. 4A, 4B), post-processing. The cell bed lower surface 20s can reside against the base surface 11i or may reside a distance above the base 11 attached to an inner surface 10s of a sidewall 10w of the tube 10.

Figure 4B:
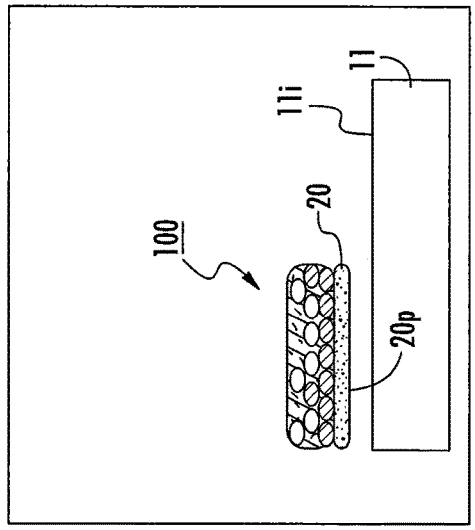
FIGS. 4A-4C are schematic illustrations of an exemplary sequence of post-processing, cell block removal operations that can be carried out according to embodiments of the present invention.

The internal base surface 11i can include a non-stick material and/or coating that reduces sliding friction and/or otherwise facilitates the removal of the cell bed 20 from the base 11 with the cell block 100 (FIG. 4C) for conventional cell evaluation after processing. In some embodiments, the cell bed 20 with the cell block 100 can be pushed off the base or pushed up and out of the tube body once the base is removed. Optionally, a thin flexible liner 110 (FIG. 4C) can reside on the surface 11i to allow the cell block 100 to be lifted or more readily slid off the base 11 (FIG. 4C). The liner 110, where used, can be adhesively attached to the internal surface of the base 11i and a user can lift to peel an edge and dislodge the cell block 100.

The cell bed 20 can be a monolithic solid layer of an inert material. In other embodiments, the cell bed 20 can comprise a plurality of stacked layers of different solid materials or a mixture of materials. The cell bed 20 can comprise paraffin or other suitable material alone or in combination with one or more other materials. In some embodiments, the cell bed 20 is defined by a monolithic paraffin body. In some embodiments, DNase and/or RNase inhibitors may be added to the fixative or other liquid solutions and/or paraffin that may improve future molecular testing.

In some embodiments, the base 11 is detachable, e.g., releasably attachable to a bottom portion 10l of the tube 10. This releasable attachment can be by any suitable attachment configuration including, for example, threaded attachment, bayonet or frictional fit, snap fit, hooks, VELCRO, adhesive attachment, frangible attachments, any of which may optionally also employ O-rings, compatible sealant, wax or grease or washers to promote a sufficient fluid-tight seal. For frangible attachments, the tube body 10b and/or base 11 can be integrally attached and configured to preferentially tear or detach about a defined zone when exposed to sufficient compressive, torsion or tensile forces.

The tube 10 can be provided in a sterile package 40 for onsite collection of a specimen from a patient. The term "onsite" refers to a collection location of a patient such as a surgical or biopsy room, doctor's office or hospital or laboratory site. The tube 10 can include a lid or cap 12 (FIG. 2C) that is provided in the package 40 or in a separate package. In other embodiments, non-sterile uses are contemplated.

The base 11 can be provided in the package 40 preassembled or pre-formed in the tube 10 and/or base 11 as shown. Alternatively, it may be provided separately for attachment at the use (collection) site (FIG. 11). As such, the cell bed 20 may be provided as a separate component in the package 40 or a separate package (held in a rigid container so as to protect the preformed shape). In other embodiments, the cell bed 20 is pre-assembled into the base 11 or bottom 10l of the tube body 10b. In some particular embodiments, the cell bed 20 can be formed in the tube 10 at the collection site if a suitably reliable press or formation system can be included in a collection kit.

Figure 2A:
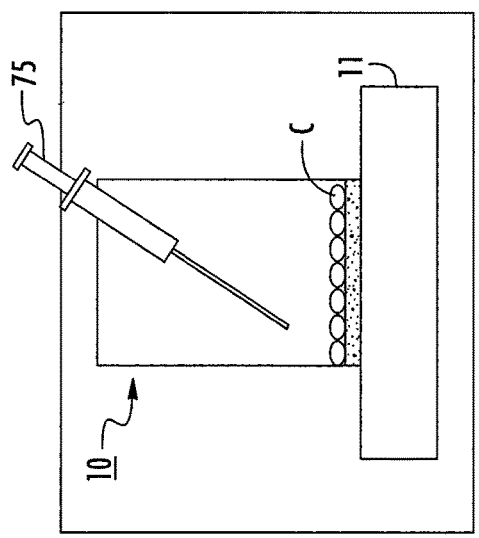
FIGS. 2A-2C are schematic illustrations of an exemplary sequence of cell collection operations that may be used with biosample containers according to embodiments of the present invention.
Figure 2C:
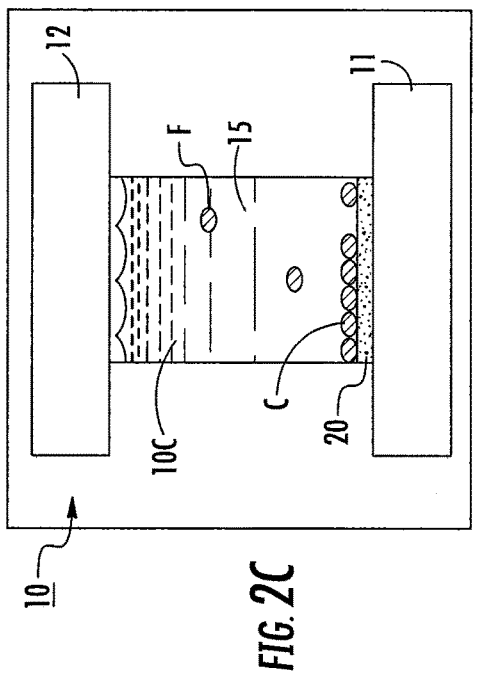
Figure 2B:
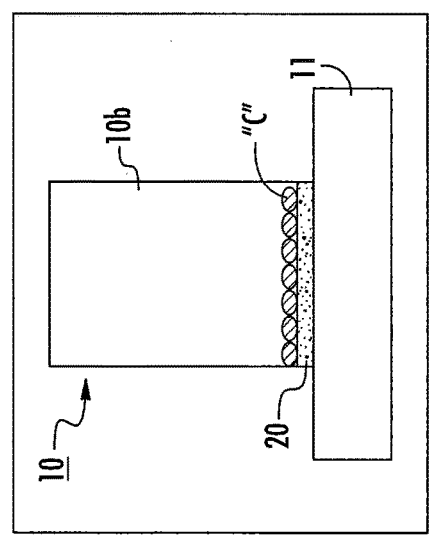

In some embodiments, the cell bed 20 can be pre-formed in the tube 10 with a defined three-dimensional shape, in package 40, so that the tube 10 is ready for use at a cell collection site. The package 40 can hold a single tube or multiple tubes 10. The cap 12 (FIG. 2C) can be on the respective tube 10 to maintain the sterility until use. FIGS. 2A-2C illustrate exemplary steps that can be carried out at a collection site to collect cells for subsequent evaluation. As shown in FIG. 2A, a sample with cells C is introduced into the internal cavity 10c of the tube 10 and rest on the cell bed 20. The cells C may comprise aspirated cells (unclotted) from a FNA using a needle 75 that is directly inserted into the tube 10, in some embodiments. FIG. 2B illustrates that the cells C may then clot (onsite). FIG. 2C illustrates that a supernatant, e.g., a solution of fixative liquid 15 that may comprise formalin or other suitable fixative material such as Zinc can be introduced into the tube 10. Other fixatives may include, but are not limited to, saline, alcohols, acetone, mercury based reagents, and even media (Lennox broth, RPMI, etc.). The vessel 10 can be provided unfilled and a user can select the appropriate fixative or several or a particular type may be prepackaged in a kit which may be ordered for use. Any media used in the tube body 10b should be sterilized.

A lid 12 can be attached to the tube 10 and transported or stored. As shown, there may be undesired floating cells F in the solution above the clotted cells on the cell bed 20.

The lid 12 can be a rigid closed lid that is attached after the fixative 15 is introduced. However, in some embodiments the lid 12 can include a liquid entry port to allow the liquid to enter while the lid remains on. The lid 12 can include a luer lock or luer slip connection fitting that engages with a male syringe luer lock or slip fitting to provide the liquid entry hat allows the liquid to be introduced through the port.

Figure 3A:
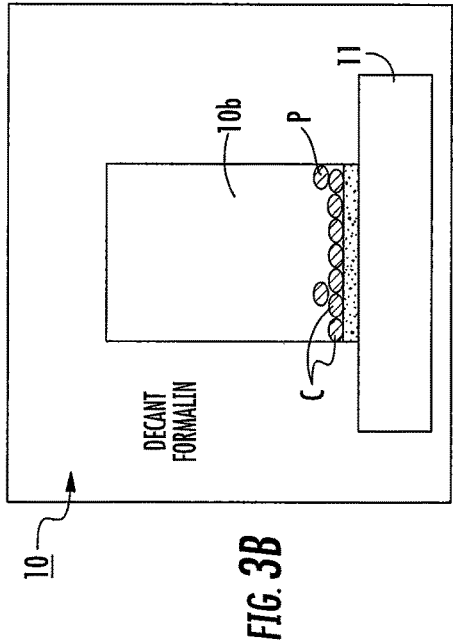
FIGS. 3A-3F are schematic illustrations of an exemplary sequence of cell processing operations that can be carried out using the biosample containers according to embodiments of the present invention.

FIGS. 3A-3F illustrate steps that can be carried out at a cytology laboratory or other suitable research or clinical laboratory. FIG. 3A shows the tube 10 after centrifugation in a centrifuge 200 (FIG. 10). The centrifuge can be a standard laboratory centrifuge, typically a low speed centrifuge that permits the separation of the fixative from the cells and allows the cells to form a cell pellet P as is known to those of skill in the art. The centrifuge may be configured to process standard 50 mL or 100 mL conical tubes and the tube 10 can be placed therein alone or with an adapter. That is, the tube 10 may include a sleeve, adapter, or coupler or may have an external integrated size and/or design that allows it to be placed directly into the "bucket" or standard receptacle of the centrifuge.

Figure 3B:
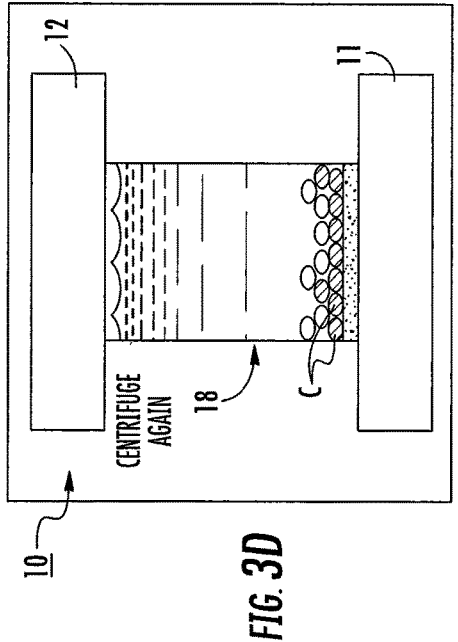
Figure 3C:
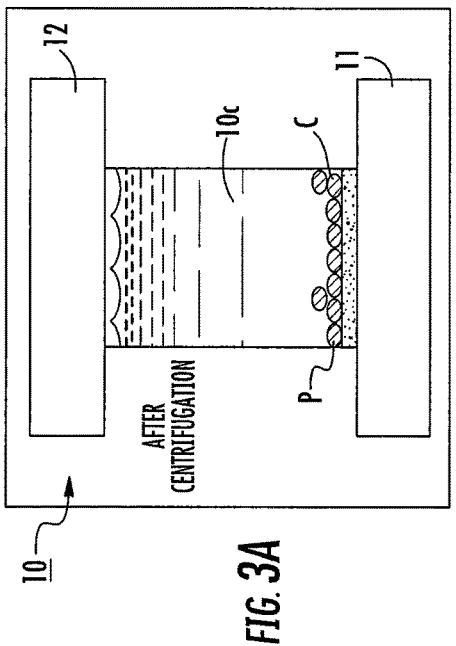

The fixative liquid 15 is removed (e.g., the formalin is decanted) as shown in FIG. 3B and a rinse solution 18 can be added to the tube 10 as shown in FIG. 3C. The fixative liquid 15 can be removed and the rinse 18 added via any suitable technique that leaves the cells C and/or pellet P in the tube 10 including aspiration tubing, pipette withdrawal, decanting and the like. Typically, the supernatant should be aspirated gently with a vacuum rather than being decanted (which refers to tipped and poured) to minimize or reduce trauma to the cell pellet. As before, the rinse solution or other liquids can be removed or added with the lid 12 off as shown in FIG. 3B or with the lid remaining on the tube using a liquid entry and/or retraction port. It is also contemplated that different lids having the same or different configurations may be used at different points in the process.

In some embodiments, a clot blot formed during the collection/post-collection can be used as a cap for a rinse vessel.

Figure 3D:
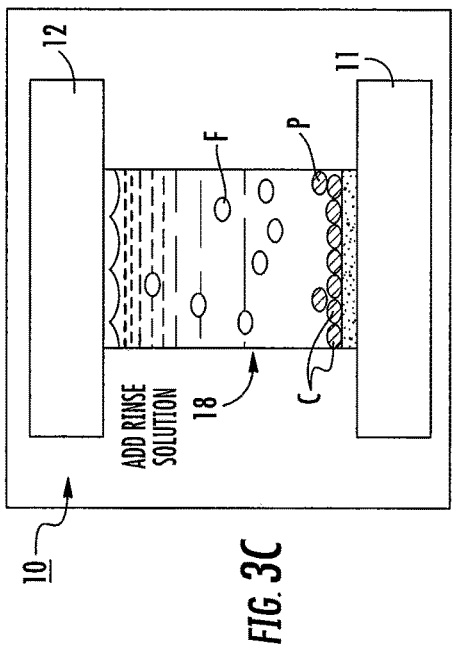
Figure 3F:
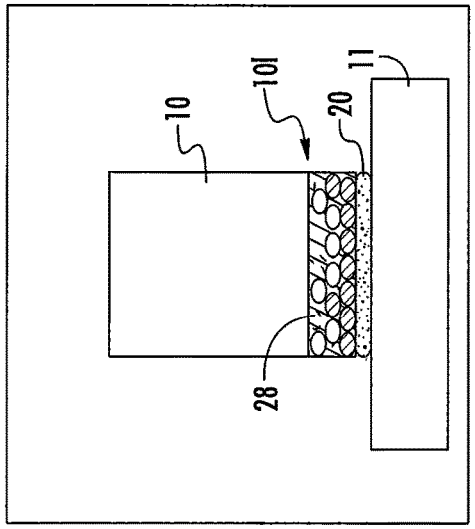
Figure 3E:
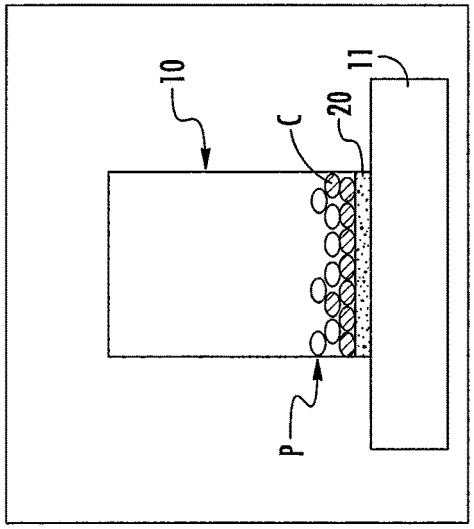

FIG. 3D illustrates that the tube 10 with the rinse 18 can then be centrifuged. FIG. 3E illustrates that the rinse 18 can be decanted or otherwise removed or withdrawn, leaving cells C on the cell bed 20, typically in pellet form P. FIG. 3F illustrates that a matrix material 28 can be added to form a cell block 100. The term "matrix material" refers to a specimen-processing gel (that may be aqueous) that encapsulates and suspends histologic and cytologic specimens in a solidified medium. The matrix material 28 can include one or more of agar, agarose gel or "histogel" solid at ambient temperature, Methocell®, Matrix Gel®, OCT compounds, paraffin, denatured and non-denatured collagen, fibronectin, laminin, plasma and thrombin and other mixtures. Other matrixes for cell immobilization can also be used. For a discussion of cell blocks and ethanol formalin fixative and other fixatives, see, e.g., Nathan et al., *Improved Preparation and Its Efficacy in Diagnosing Cytology*, Am J Clin Pathol, 2000; 1114, 599-606, the contents of which are hereby incorporated by reference as if recited in full herein.

Figure 4A:
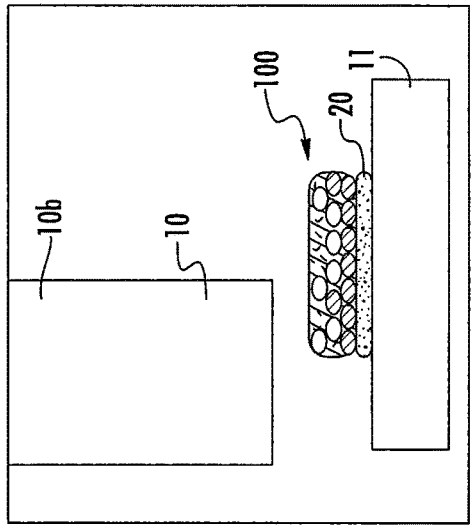
Figure 4C:
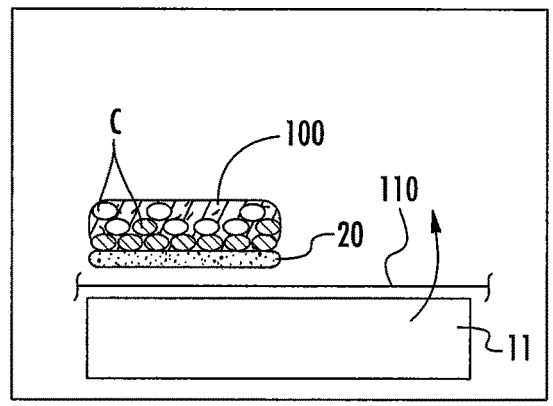

FIG. 4A illustrates that the base 11 and body of the tube 10b are detached from each other, exposing the cell block 100 on the cell bed 20. The cell block 100 with the cell bed 20 are removed from the base 11 as shown in FIG. 4B. The cell block 100 with cell bed 20 can be detached, removed or separated in any suitable manner including, for example, scraping, sliding or lifting (e.g., using a liner 110, FIG. 4C).

Figure 5:
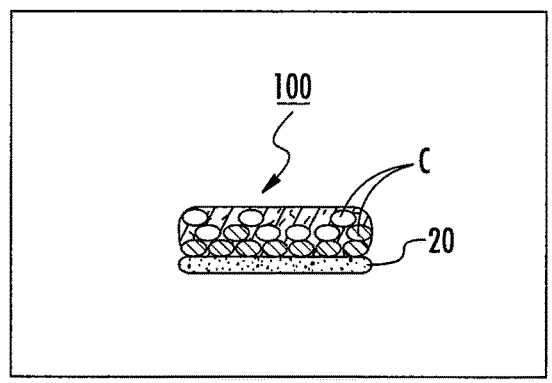
FIG. 5 is a schematic illustration of a finished cell block (e.g., cell disk) on the cell bed in the containers shown in FIGS. 2A, 3A and 4A according to embodiments of the present invention.

FIG. 5 illustrates the resulting cell block 100 (also termed cell disk) that includes the cell bed 20 ready for routine processing. The cell block 100 can be sliced or cut for preparing slides for staining or other diagnostic protocols. There may be an increased number of cells in the cell block or slices thereof that may promote diagnostic capability over smears alone.

Figure 6A:
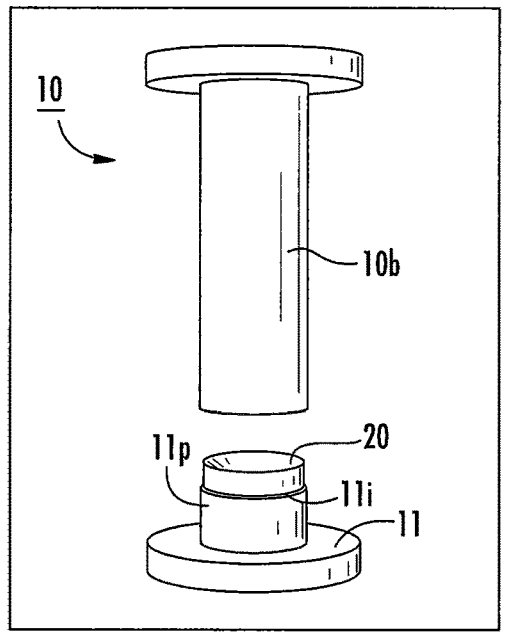
FIG. 6A is a partial exploded view of another example of a container according to embodiments of the present invention.

FIG. 6A illustrates the tube 10 with the base 11 detached from the tube body 10b. In this example, the base 11 includes a raised center pedestal 11p that forms the inner surface 11i that holds the cell bed 20. The perimeter of the pedestal 11p can include threads that engage an inner surface of the tube body or may frictionally engage the tube body using seals such as an O-ring(s) and the like (not shown).

Typically, the base 11 with the cell bed 20 on the pedestal is attached to the tube body 10b and packaged for use at a collection site.

FIG. 6B illustrates that the tube 10 can include a spacer 13 that rises a distance above the lower portion of the base 11. FIG. 6B also illustrates that the base 11 can attach to the tube body 10b at a location above the bottom of the base 11. The spacer 13 can include a substantially planar or flat surface for holding the cell bed 20. The base 11 and tube body 10b can threadably couple together. In the embodiment shown, the base 11 includes external threads 34 and the tube body 10b includes internal threads 38. However, as noted above, other coupling configurations may be used.

FIG. 6C illustrates that the base 11 can interchangeably attach to two different tube bodies $10b_1$, $10b_2$, and/or the different tube bodies can have different volumes. Thus, for example, the smaller tube body $10b_1$ can be used at the collection site and for transport to the cytology lab. The larger tube body $10b_2$ can be used at the cytology lab for processing in the centrifuge, for example. The same or differently configured caps or lids 12 may be used for each tube body $10b_1$, $10b_2$. In other embodiments, different volume tube bodies $10b_1$, $10b_2$ can be provided in a package and selected for use at the collection site allowing for increased flexibility corresponding to the specimen type (e.g., urine, blood plasma or serum versus FNA).

FIG. 6D illustrates that the tube body 10b can include several segments $10b_1$, $10b_2$ that attach together to provide a different volumetric capacity. Thus, for example, one segment $10b_1$ can be attached and used with the cap or lid 12 at the collection site and for transport. The lid/cap 12 can be removed and the second body $10b_2$ can be attached to the first body $10b_1$ at the cytology lab and the stacked segments can define the tube body 10b used for centrifugation. Where more than one tube body segment $10b_1$, $10b_2$ is used, one or both can be detached from each other and/or the base 11 to expose the cell bed 20 with the cell block 100 for access/removal of the cell block 100 for subsequent processing and analysis.

Figure 7A:
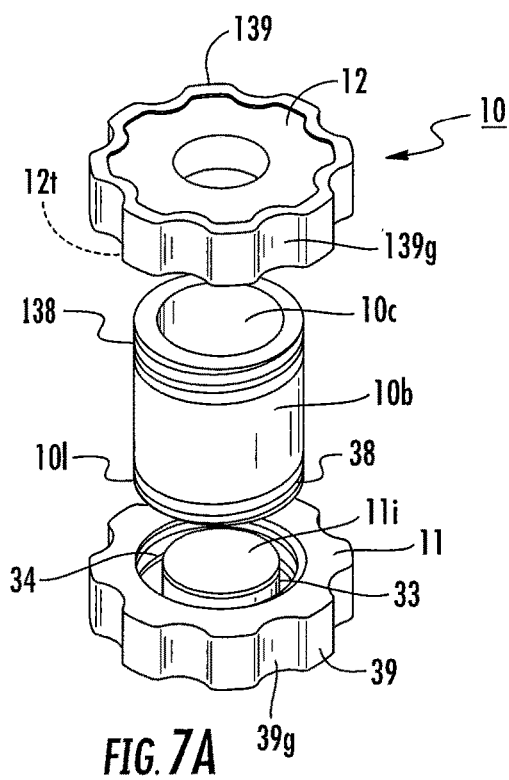
FIG. 7A is a side perspective view of another example of a biosample container according to embodiments of the present invention.
Figure 7B:
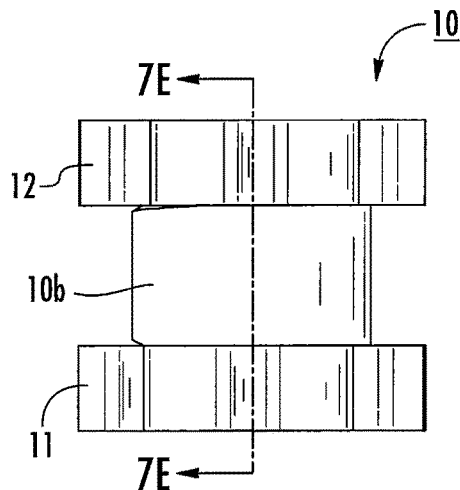
FIG. 7B is a side view of the device shown in FIG. 7A.
Figure 7C:
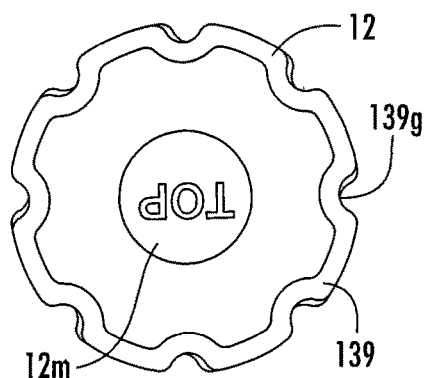
FIG. 7C is a top view of the device shown in FIG. 7A.
Figure 7D:
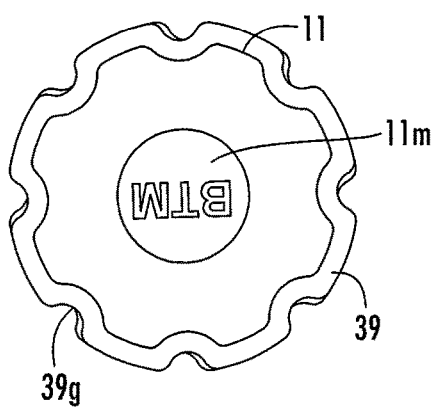
FIG. 7D is a bottom view of the device shown in FIG. 7A.
Figure 7E:
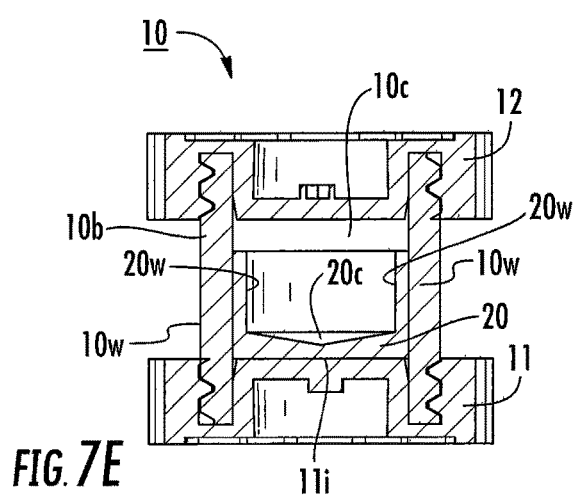
FIG. 7E is a section view taken along lines 7E-7E in FIG. 7A.

FIG. 7A is an exploded view of another example of a tube 10. In this example, the base 11 has an annular open space 33 with female threads 34 that surrounds the internal surface 11i that holds the cell bed 20. The female threads 34 matably engage external male threads 38 on the bottom portion of the tube 10l.

FIGS. 7B-7E illustrate that the tube 10 can include top and bottom indicia 12m, 11m so that a user knows which end is "up" before using or opening. In some embodiments, a visually transparent window may be provided in the tube or cap or base or the device may be transparent or translucent. The cell bed 20 can have a substantially conical shape with the lowest peak facing the base 11 along an axially projecting centerline of the tube body 10b. The outerwalls of the cell bed 20w can extend above the center portion of the cell bed 20 in a substantially straight vertical orientation so as to conform to the sidewalls of the tubular body 10b. The sidewalls 20w can cover more than a major portion (e.g., greater than 50%) of the enclosed fluid cavity 10c, leaving a minor portion of the sidewalls 10w of the tube body 10b below the cap 12 free of the cell bed material.

The tube 10 can have a defined capacity or volume. The tube 10 may have a volume or capacity between about 10 mL to about 200 mL, including about 20 mL, about 30 mL, about 40 mL, about 50 mL, about 60 mL, about 70 mL, about 80 mL, about 90 mL, and about 100 mL. The tubes 10 can be provided in different volumes/sizes for different applications. Where two segments $10b_1$, $10b_2$ are used, one can have a volume between 10 mL to 25 mL and the other can have a volume between 25 mL and 100 mL, for example.

The lid 12 can also be threadably attached to an upper portion of the tube body 10 via threads 12t, 138. The base 11 and cap 12 can have a ledge 39, 139 with a diameter that defines a tight fit with a receptacle of a standard centrifuge or with a standard tube, sleeve or other adapter allowing the tube 10 to be placed in a centrifuge for processing.

The cap and base ledges 39, 139 can be configured to have the same outer diameter size. The outer perimeter of the ledge can include a pattern of circumferentially spaced apart recesses or grooves 39g, 139g. The ledges 39, 139 can provide a resilient fit to provide for snug engagements using an overcoat, outerlayer or substrate of resilient material or just based on the groove configurations.

In some embodiments, the tube 10 is sized and configured as a 50 mL tube and can snugly engage a centrifuge receptacle without the use of an adapter or without a customized sleeve or other adapter.

Figure 8A:
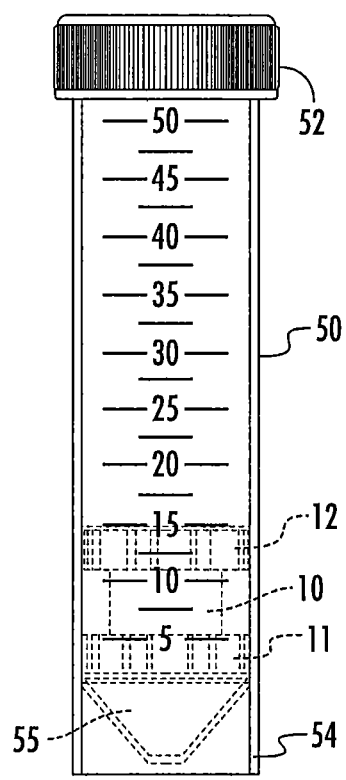
FIG. 8A is a front view of a container assembly that holds a collection container with the integrated cell bed therein according to embodiments of the present invention.
Figure 8B:
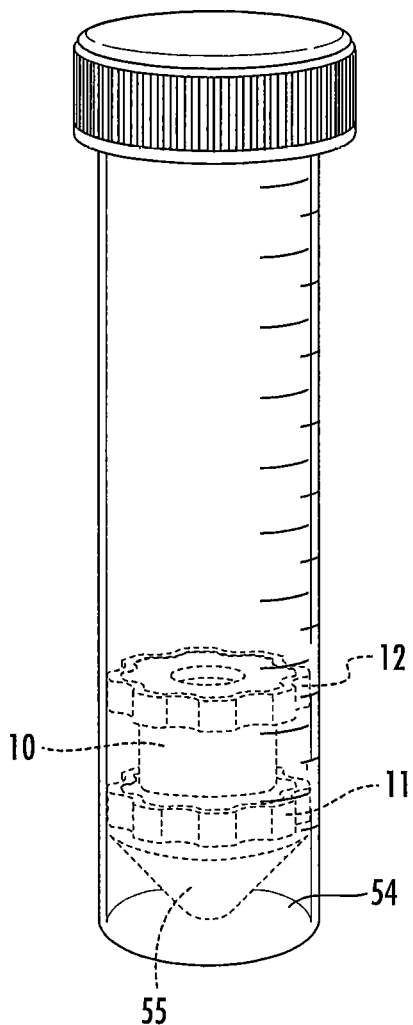
FIG. 8B is a front perspective view of the container assembly shown in FIG. 8A.

FIGS. 8A and 8B illustrate that the tube 10 can be placed inside a larger (standard) tube 50 for standard centrifuge processing. The ledges 39, 139 can snugly engage the sidewall of the tube 50. The tube 50 can include a cap 52 and the lower portion 54 can include a center with a conical internal shape 55. The tube 10 typically resides over the conical shape in the bottom portion of the standard tube 50. However, the tube 10 can be placed above this location as well. The tube 10 can be slid in and out of the tube 50 for access.

Figure 9A:
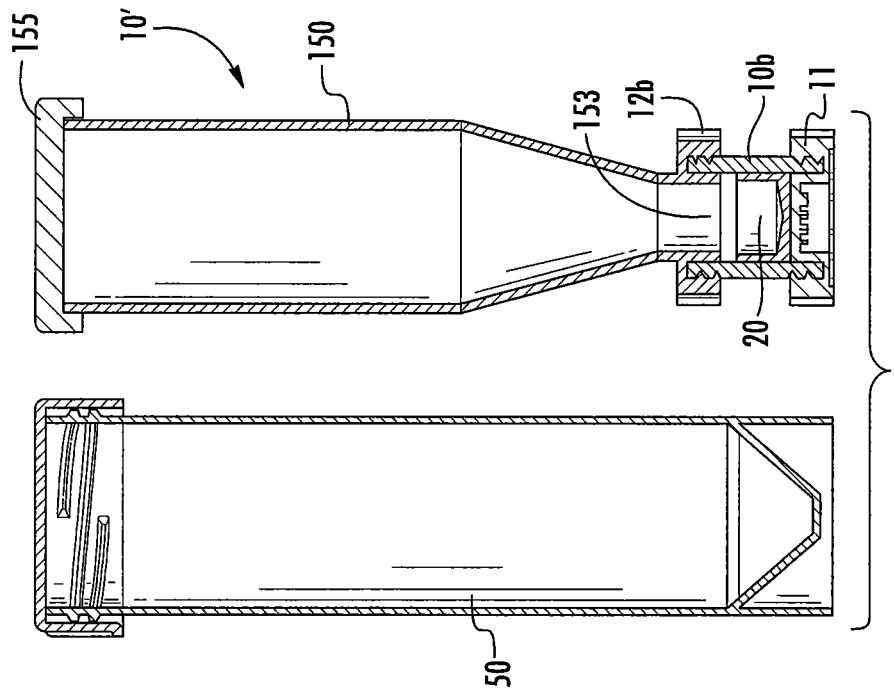
FIG. 9A is a front view of a biosample tube having an alternate top or cap configuration according to embodiments of the present invention.
Figure 9B:
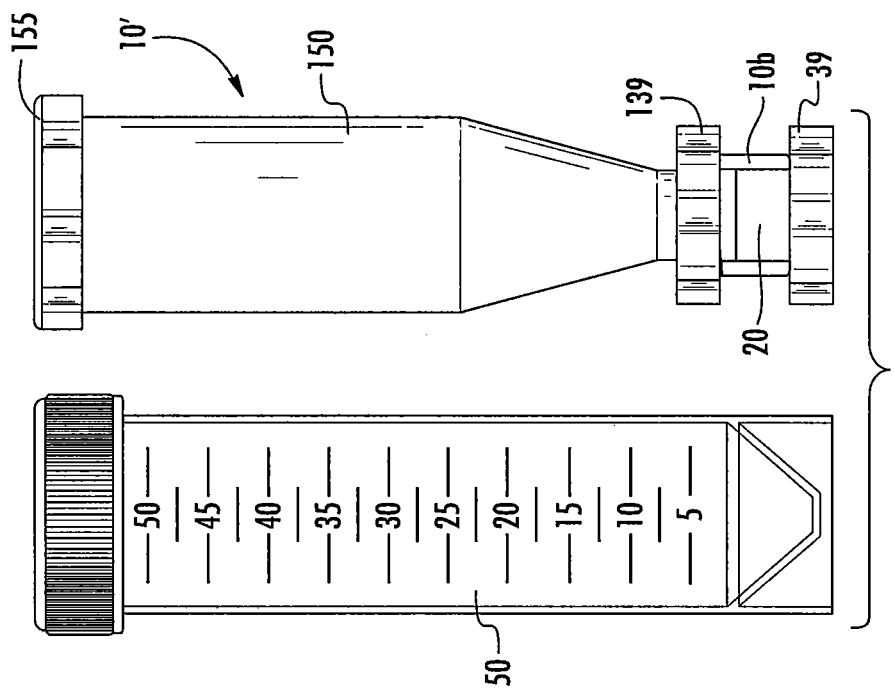
FIG. 9B is a sectional view of the device shown in FIG. 9A.
Figure 9D:
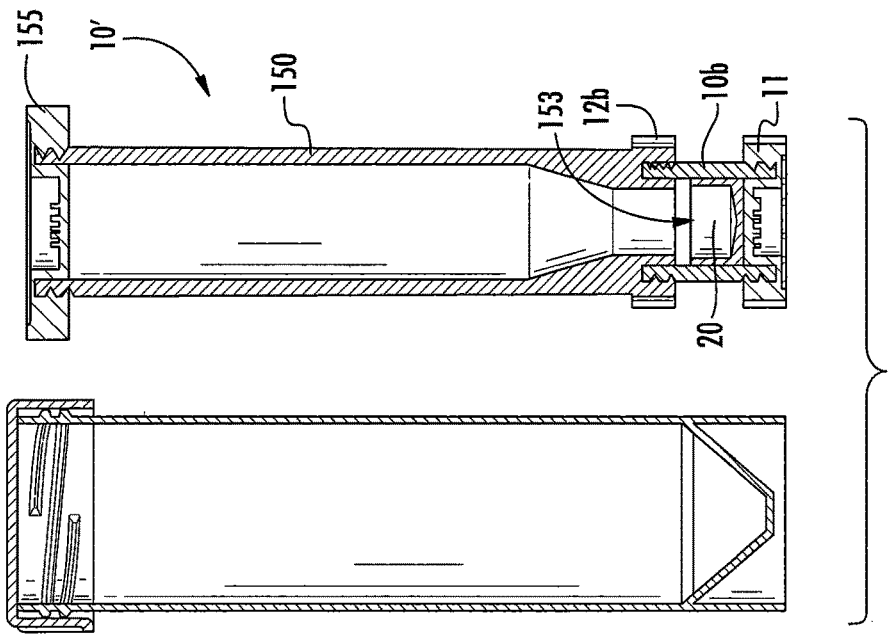
FIG. 9D is a sectional view of the biosample tube shown in FIG. 9C.
Figure 9C:
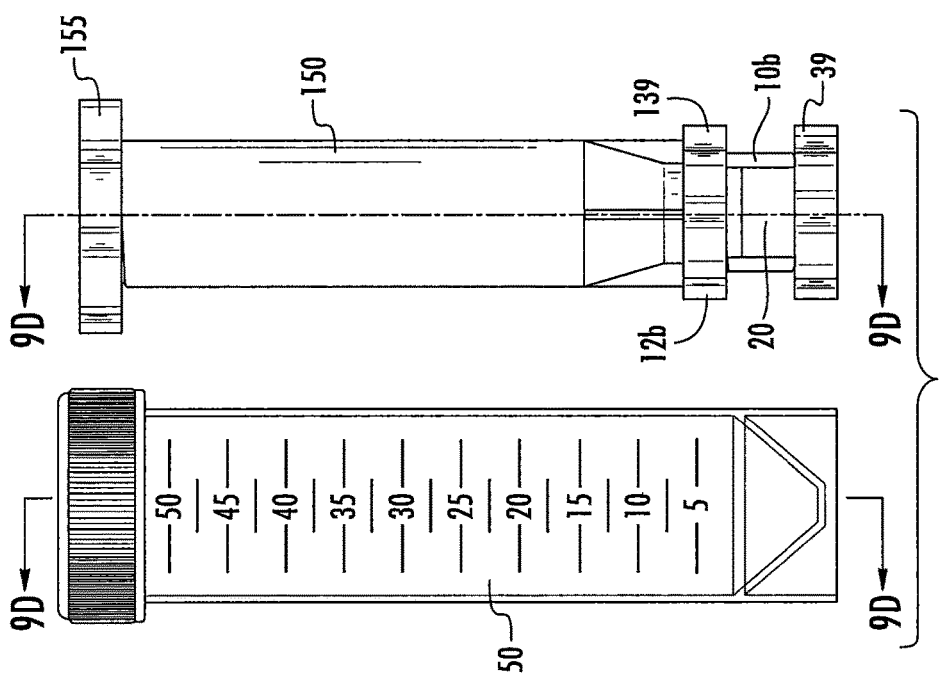
FIG. 9C is a front view of a biosample tube similar to that shown in FIG. 9A, having an alternate top configuration for processing according to embodiments of the present invention.

FIGS. 9A and 9B illustrate another embodiment of a container 10' where the tube body 10b can releasably attach to an elongate body 150 which may be attached to a second cap 12b. As shown, the elongate body 150 is in fluid communication with the tube fluid cavity 10c. The second tube cap 12b can define a fluid port 153 that allows fluid from the elongate body 150 to be introduced or withdrawn. The tube body 10b with the second cap 12b can be configured to reside in a standard 50 mL tube 50 as shown. In other embodiments, the tube body 10b and second cap 12b can be configured to snugly reside in a centrifuge receptacle (e.g., bucket) without requiring the tube 50. The elongate body 150 can be integral with the tube cap 12b, e.g., a monolithic molded unitary component. In other embodiments, the elongate body can be configured to attach to the lid 12b in other ways including threaded, snap fit and the like, while providing a fluid-tight seal. FIGS. 9C and 9D illustrate a similar configuration of a container 10' with an alternate top configuration. In some embodiments, the elongate body 150 may be attached at the collection site as the original cap. In other embodiments, a cap or lid 12 such as that shown in FIG. 7A can be used at the collection site and/or for shipment and transport and the second cap 12b or elongate body 150 interchanged later for processing.

Figure 10A:
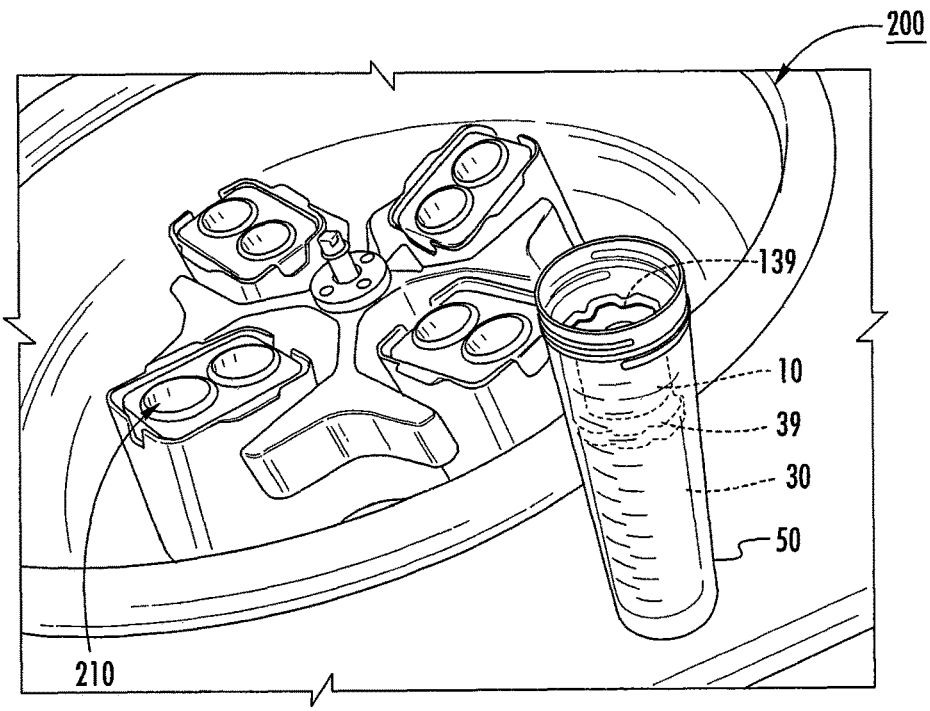
FIG. 10A is a front perspective view of the container assembly (sans upper lid) adjacent an exemplary centrifuge according to embodiments of the present invention.
Figure 10B:
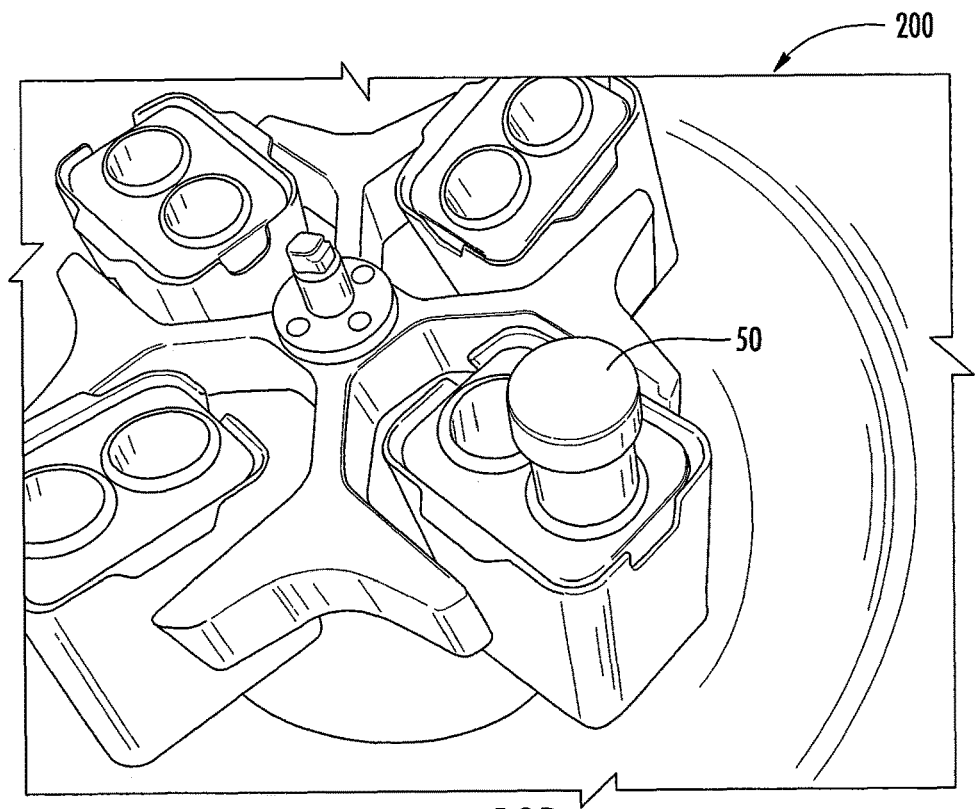
FIGS. 10B and 10C are top perspective views of the container in position in the centrifuge according to embodiments of the present invention.
Figure 10C:
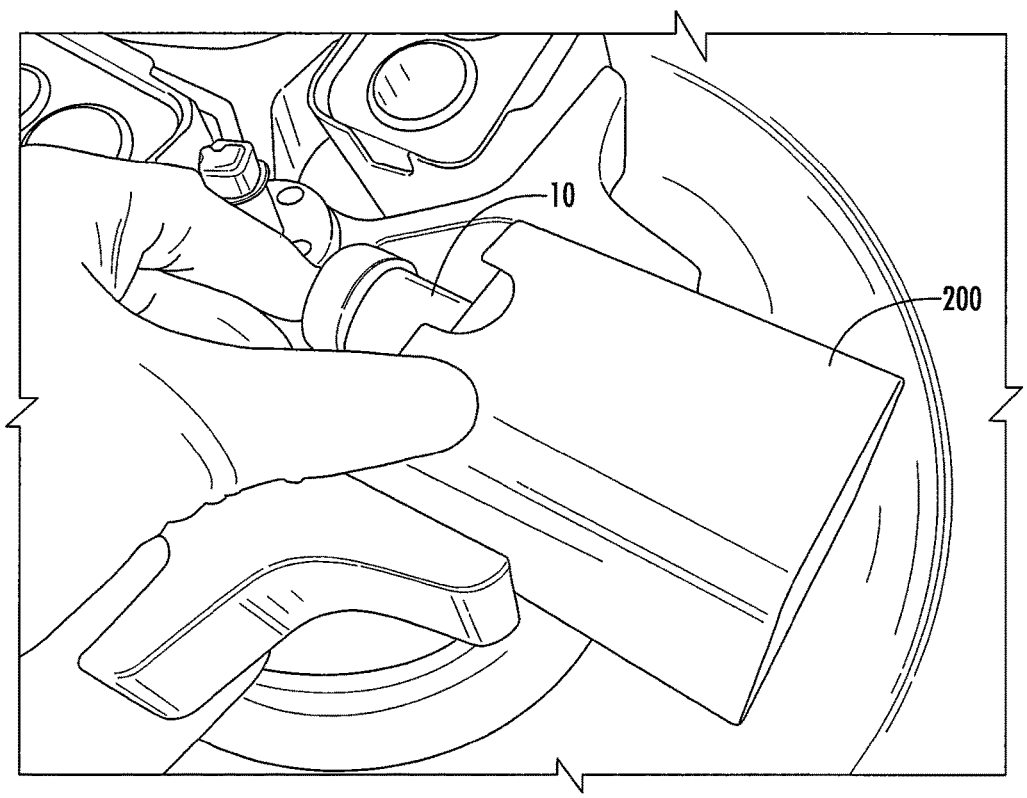

FIG. 10A shows the tube 10 sitting over a spacer 30 snugly attached to and in a standard 50 mL tube 50 in preparation for centrifugation in a bucket 210 of the centrifuge 200. FIG. 10B illustrates the tube 10 in the tube 50 in a standard swing bucket 210 of the centrifuge 200. FIG. 10C illustrates centrifugation with the tube 10 on its side (and horizontal) rather than angled so that the specimen is collected in a middle 20c (FIG. 1B) of the cell bed 20.

FIG. 11 illustrates the components of a tube 10 according to some embodiments. As noted above, the cell bed 20 can be pre-formed and provided for assembly onsite or may be pre-attached to the base 11 and/or tube body 10b. Typically, the base 11 with the cell bed 20 is attached to the tube body 10b and packaged for use at a collection site.

FIG. 12 illustrates that the cap 12' can be configured to engage a leur-lock of a syringe 120 for introducing and/or removing different liquids.

Figure 13B:
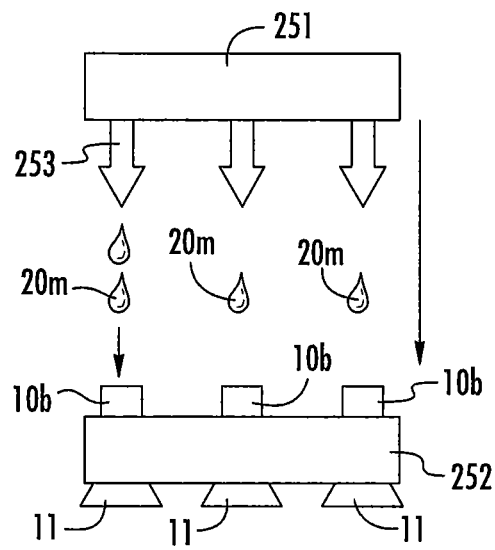
FIG. 13B is a schematic illustration of another forming apparatus according to embodiments of the present invention.
Figure 13C:
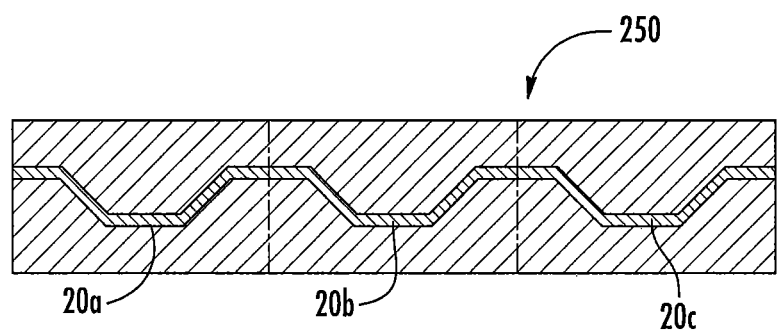
FIG. 13C is a section view taken along lines 13C-13C in FIG. 13A.

FIGS. 13A and 13C illustrate examples of a mold that has mold cavities $20c_1$-$20c_n$ that can concurrently form a plurality of cell beds 20. Cell bed material, in liquid, solid, or semi-solid form, typically in flowable (fluid or gel) form can be introduced into the mold via one or more mold ports or through an open access region and molded into the preformed cell bed shape for use in the tube 10.

In some embodiments as shown in FIG. 13B, a mechanical press 251 with shaped mold members 253 can be configured to enter the tube body 10b with an attached base 11 held in a lower holding member 252 to allow concurrent cell bed formation in multiple tubes 10. The cell bed material 20m can be inserted in solid or liquid form, typically in a solid, but perhaps slightly heated form for aid in formation of the desired cell bed shape.

Figure 14:
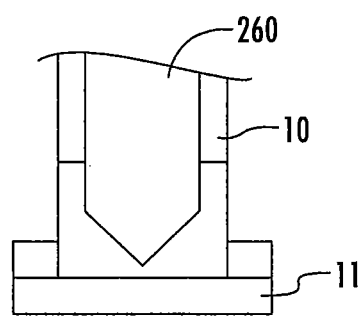
FIG. 14 is a schematic partial section view of yet another cell bed forming device according to embodiments of the present invention.

In other embodiments, as shown in FIG. 14, a respective cell bed 20 is formed directly in an attached base 11 and tube body 10b using a shaped tamper tool 260.

In some embodiments, the tubes 10 can be used to process cells for human or veterinary uses. In certain embodiments, the tubes 10 can be directed to preparation of cells for pathology review. While it is contemplated that the tubes 10 are particularly suitable for cells obtained by fine needle aspiration, it should be clear to one of skill in the art that cellular material captured by other means could also be collected and processed by the tubes 10.

Cell material could also be collected by endoscopy, including but not limited to arthroscopy, bronchoscopy, colonoscopy, colposcopy, cystoscopy, ERCP (endoscopic retrograde cholangio-pancreatograthy), EGD (esophogeal-gastroduodensoscopy), endoscopic biopsy, gastroscopy, laparoscopy, laryngoscopy, proctoscopy and thoracoscopy. Cells could also be obtained from lavage procedures, including but not limited to bronchoalveolar, breast ductal, nasal, pleural, peritoneal, gastrointestinal, arthroscopic, and urinary bladder lavages. It is also contemplated that cells could be collected from catheters such as those used in infusion, cardiovascular, renal, bladder, urethral, hemodynamic monitoring, neurological, and other procedures which would be obvious to one of skill in the art. In some embodiments, cell samples can be from eye/cornea/globe aspirations, endocervical/ectocervical/endometrial curettages, cyst aspirations and urine. It is also contemplated that cell samples can be for xenografts from research and animal modeling as well as patient directed therapy.

The cells can be from washings and spontaneously exfoliated specimens including bronchial washings, bronchoalveolar lavage, sputum pleural fluid, pericardial fluid, peritoneal fluid, peritoneal washing, ovarian cyst fluid, synovial fluid, urine, brain cyst fluid, cerebrospinal fluid. The cells can be for RNA/DNA research or analysis and may include live cells. With the use of appropriate media, the tubes 10 can act as a small incubator to keep cells alive (at least for a short period of time). DNase/RNase inhibitors can be introduced to the media to also preserve DNA/RNA. As is known, fixation alone can help with DNA/RNA preservation.

In particular embodiments, the cell samples are from endocervical curettages (ECC). In the past, conventional practice when the first slide from the original paraffin block is essentially noncontributory, is to take the fluid remaining in the specimen jar and perform a "ThinPrep" on it. These typically have many cells (squamous and glandular) but there is no architecture. Rather than place the minimal slime usually present in a specimen jar in a cassette, it is contemplated that those cells can be put in the tubular body 10b (or 150, FIG. 9A, 15A) at the collection site. This should give better initial yield with architecture present and a source for immunos. This latter may not be inconsequential. For example, when the ECC contains a minute fragment of small cells with high N/C ratios, it is hard to discern whether they are not relevant (being potentially from the lower uterine segment) or clump of HGSIL cells. A single immuno—p16—can be very useful in this scenario. The term "immuno" and plurals thereof refer to immunoperoxidase studies and include antibodies targeting specific epitopes to aid in tumor/disease differentiation. Also known as (although technically incorrect) immunohistochemistry: p16 is a protein/antigen with the p16 antibody in a cell having clinical significance.

Figure 15A:
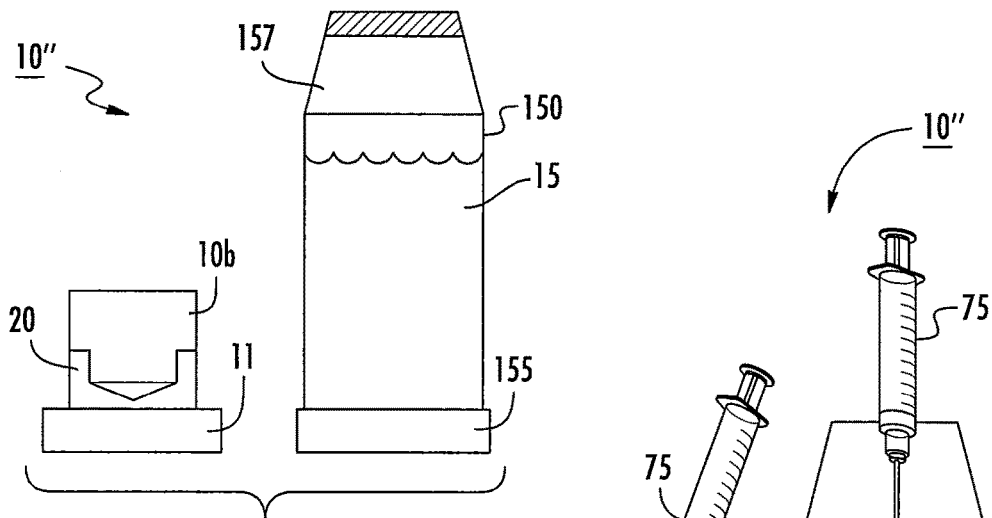
FIGS. 15A-15I are schematic illustrations of a sequence of operations that may be used to carry out embodiments of the invention and also illustrating another embodiment of a container according to embodiments of the present invention.
Figure 15B:
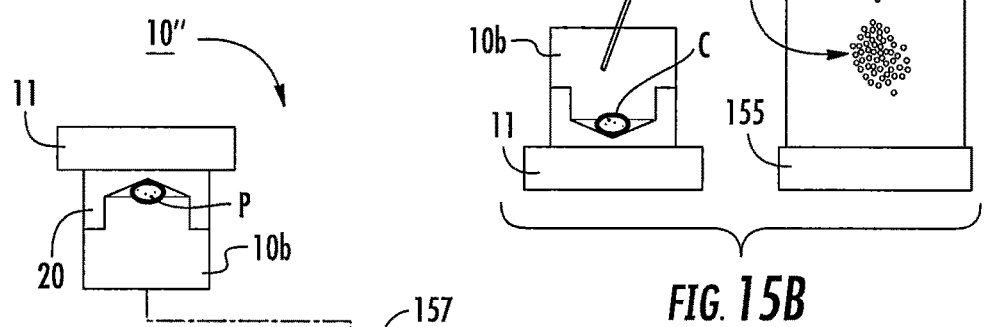
Figure 15C:
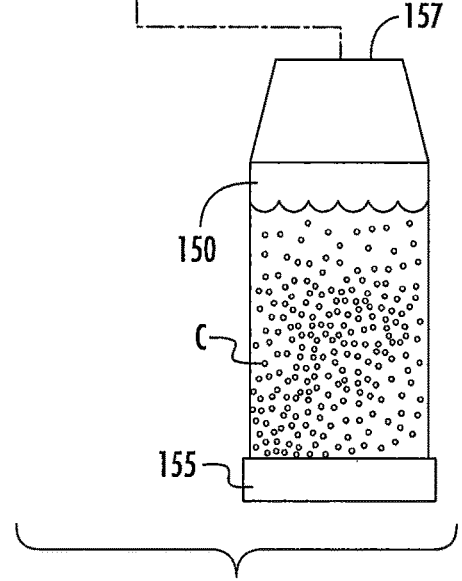
Figure 15D:
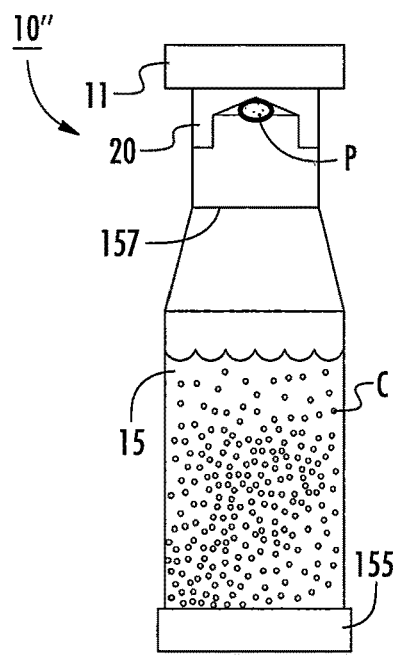

FIGS. 15A-15I illustrate another embodiment of a container 10" similar to that shown in FIGS. 9A and 9B. In this embodiment, no external tube is required for centrifuge processing. As shown, the container 10" includes a tube body 10b holding the cell bed 20 and a base 11. The container 10" also includes an elongate body 150 that can attach to the tube body 10b. The elongate body 150 can include a first end with a lid 155 and a second opposing end 157 that is open. As shown in FIG. 15A, the elongate body 150 can include a desired solution, such as saline or formalin 15. FIG. 15B illustrates that, as before, a FNA sample can be inserted onto the cell bed 20. One or more needles from other passes obtained from the target tissue can be rinsed in the chamber of the elongate body 150. This is in contrast to a jar filled with saline used conventionally. As shown in FIGS. 15C and 15D, the tube body 10b and base 11 can be attached together after the pellet P is dried allowing the tube body 10b with cell bed 20 and pellet P to be inverted to attach to the open end 157 of the elongate body 150. The open end of the elongate body 157 can be sized and configured to be substantially the same as the size of the upper end of the tube body. The elongate body 157 can taper to a large size away from the open end as shown. The tube body 10b can engage the open end of the elongate body 157 in a fluid tight manner using appropriate seals, threads, frictional fits and the like.

Figure 15E:
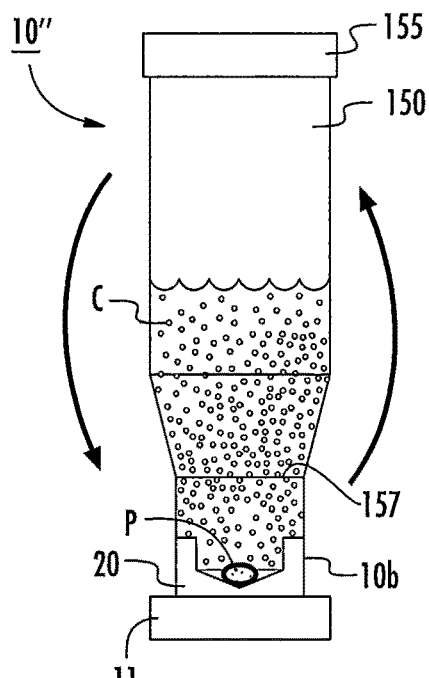
Figure 15F:
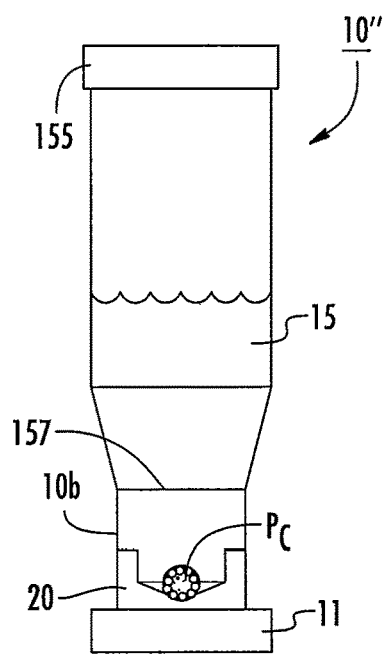
Figure 15G:
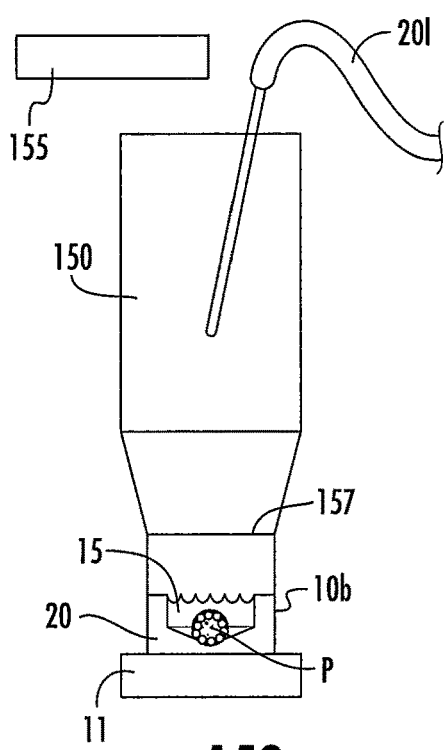
Figure 15H:
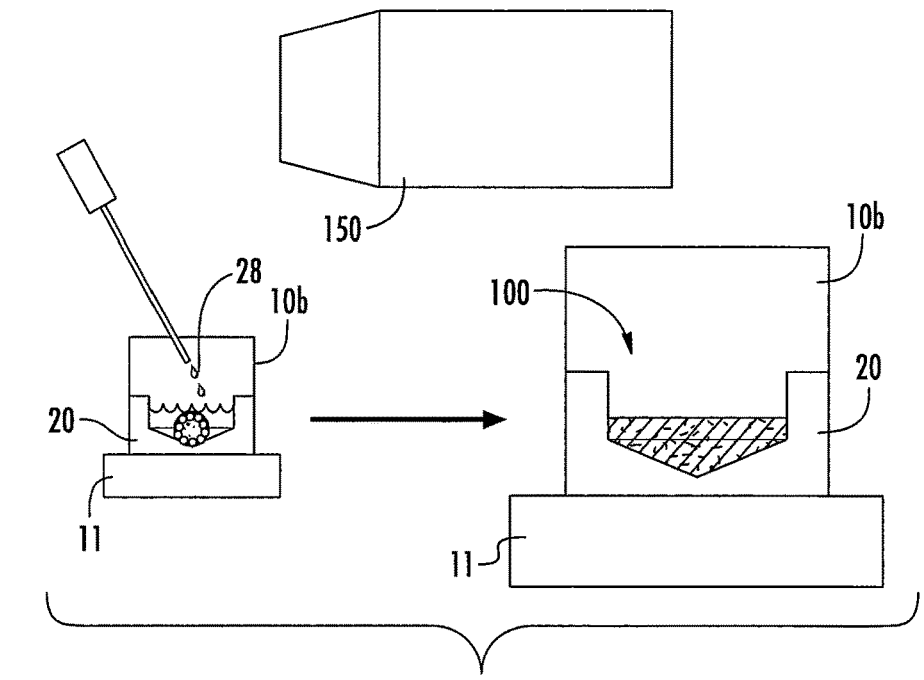
Figure 15I:
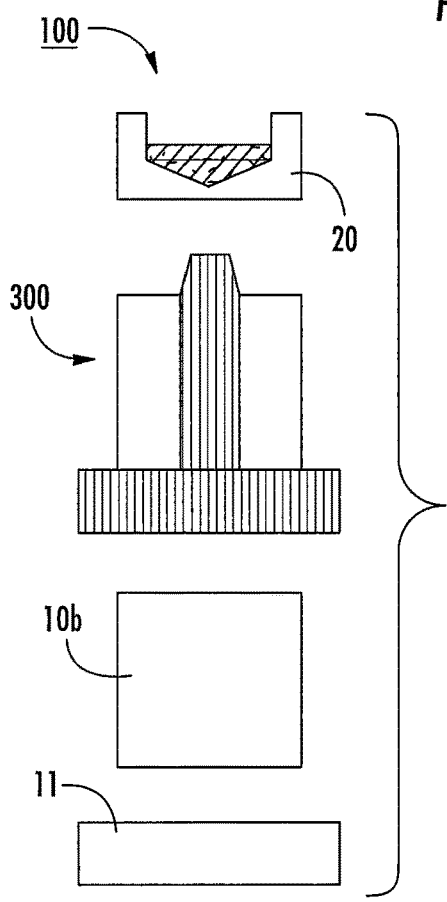

FIG. 15E shows that the container 10" can be inverted so that the cell bed 20 is in the lower portion of the container 10". The container 10" can be centrifuged at an appropriate revolution per minute and duration (e.g., about 2000 rpm for about 5 minutes) to form a combined pellet Pc (FIG. 15F) on the cell bed 20 (combined from cells collected from the rinse solution and the FNA direct deposit). FIG. 15G illustrates that the supernatant can be aspirated as is conventional using a vacuum leaving only a minimal amount of fixative 15 (e.g., formalin or saline) in the tube body 10b above the cell bed 20 so as to not disrupt the cell pellet P. The aspiration can be carried out by first removing lid 155 or by using a sealed port in the lid (not shown). As shown in FIG. 15H, the elongate body 150 can then be removed. A liquid matrix 28 can be added to the tube body 10b and cells resuspended. FIG. 15I illustrates that the cell disk or block 100 with the cell bed 20 can be removed from the tube body 10b using, for example, a plunger 300. The cell block 100 can be processed as a histology specimen or other desired specimen.

Figure 16:
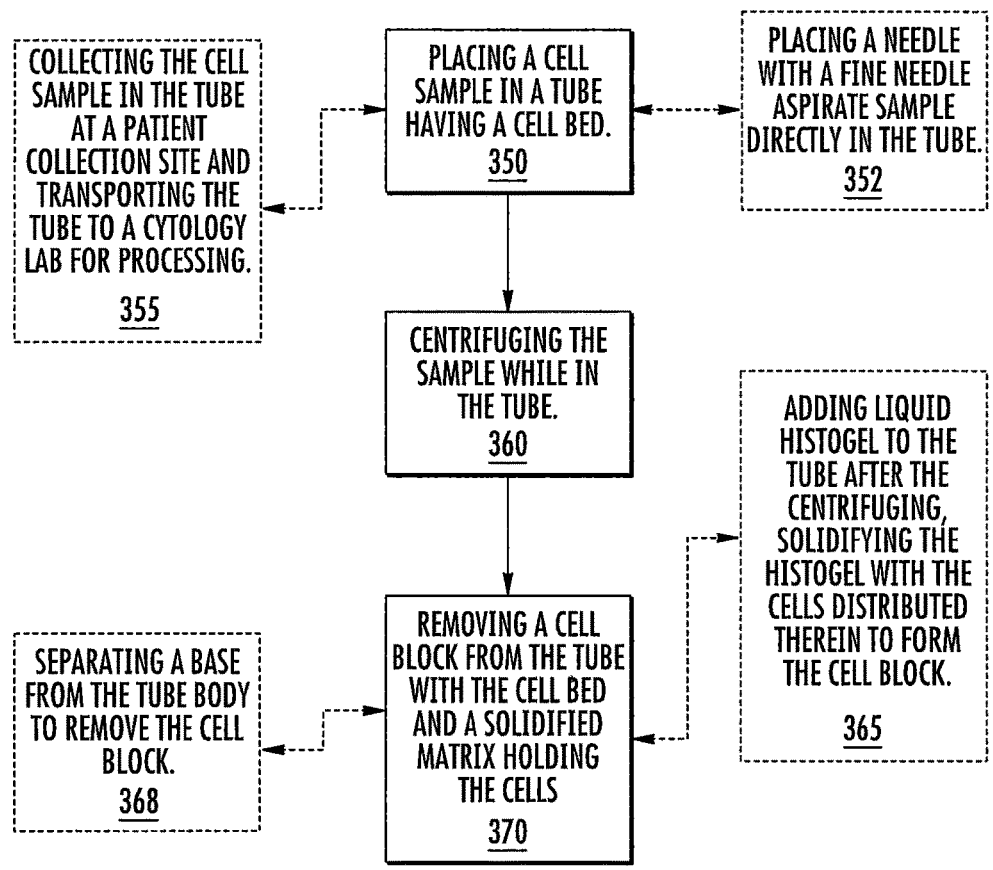
FIG. 16 is a flow chart of exemplary operations that can be used to process cells according to embodiments of the present invention.

FIG. 16 is a flow chart of exemplary operations that can be used to carry out embodiments of the invention. A cell sample can be placed in a tube having a cell bed (block 350). The sample is centrifuged while in the tube (block 360). A cell block is removed from the tube with the cell bed and solidified matrix holding the cells (block 370).

The cell sample can be placed with a needle with a fine needle aspirate sample directly in the tube (block 352). Liquid matrix material (e.g., specimen-processing gel that encapsulates and suspends histologic and cytologic specimens in a solidified medium) can be added to the tube after the centrifuging and the matrix material with the cells distributed therein can be solidified to form the cell block (block 365). The cell sample can be collected in the tube at a patient collection site and the tube can be transported to a cytology lab for processing (block 355).

The base of the tube can be separated from the tube body to expose the cell block and allow the cell block to be removed with the cell bed (block 368).

In some embodiments, generally summarized, rinses can be performed in the collection vessel 10 and the dedicated clot blot(s) can be generated as discussed above. The clot blot can be used as a cap for the rinse vessel. The entire apparatus can be inverted (clot block side down) and centrifuged. The supernatant can be aspirated leaving a clot blot with overlaying precipitated materials (button). A desired amount (not typically calculated precisely, but roughly, about 1:1/v:v to the button) of HistoGel can be pipetted onto the button and immediately spun again in a centrifuge. This time the collection vessel is not needed. This allows the HistoGel to permeate the cells and polymerize. Again, this step is carried out quickly to prevent polymerization before the centrifugation. This leaves the cells within a matrix of HistoGel. This action can prevent loss of cells in downstream processing procedures.

The present invention is explained in greater detail in the following non-limiting Examples.

EXAMPLES

Figure 17:
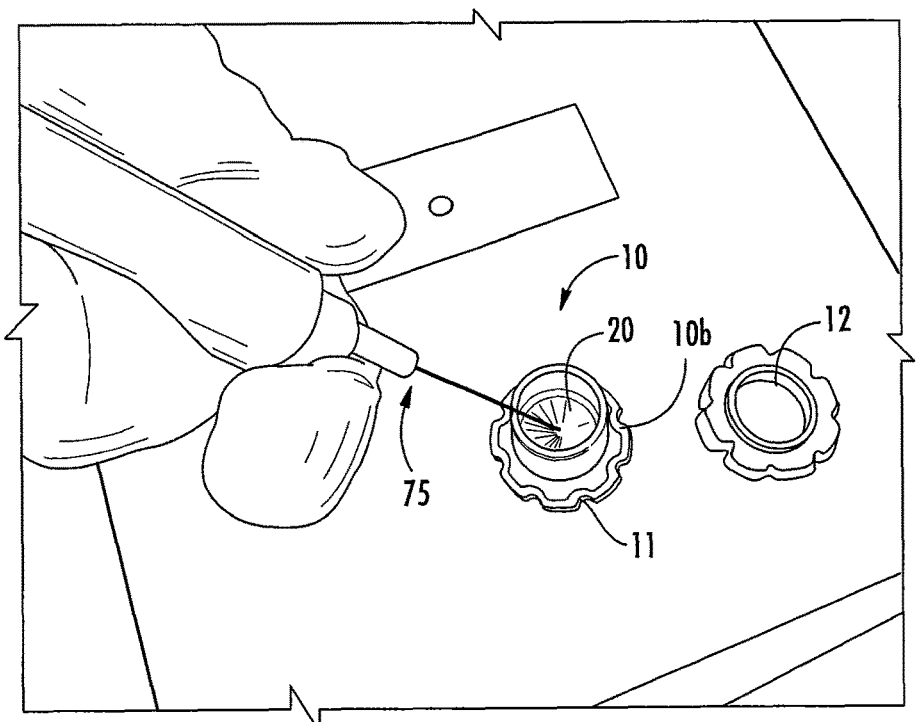
FIGS. 17-27 are digital photographs of exemplary processing steps using a collection and processing container with an integrated cell bed according to embodiments of the present invention.
Figure 18:
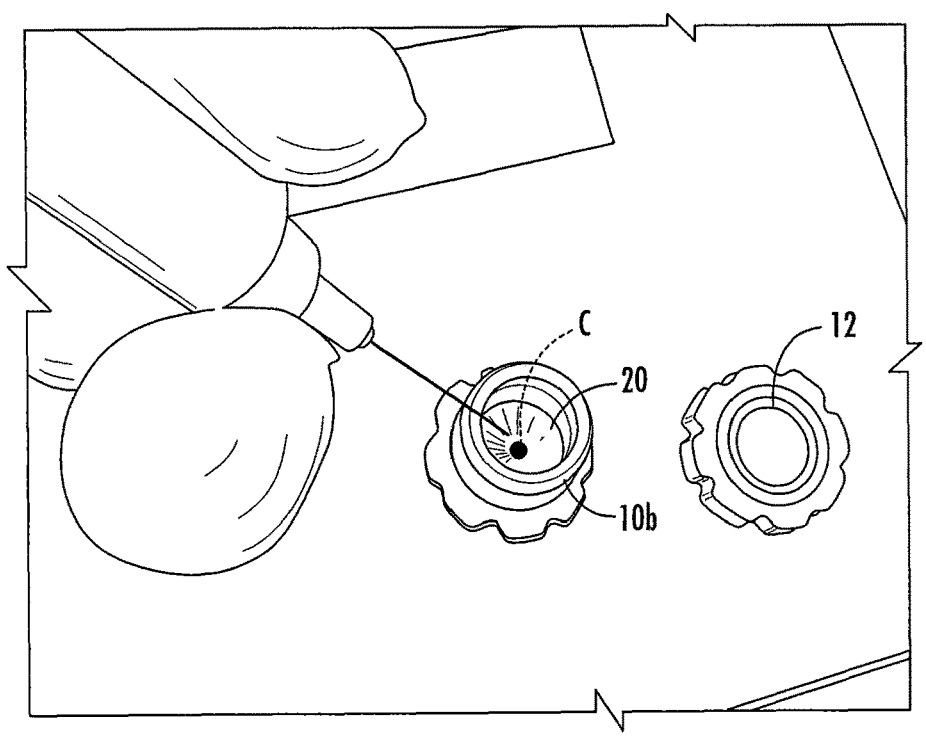

FIGS. 17-27 are digital images of an exemplary tube 10 and exemplary processing that can be carried out using the tube (the centrifuge operations were shown above with respect to FIGS. 10A-10C). FIG. 17 illustrates a FNA expelled directly from a needle into the cell bed 20 of the base 11 (which is attached to the tube body 10b). As shown in FIG. 18, the cell sample C can settle in the middle of the cell bed 20 and/or base 12 due to the substantially conical or frustoconical shape of the cell bed 20. The sample can be allowed to dry and/or coagulate.

Figure 19:
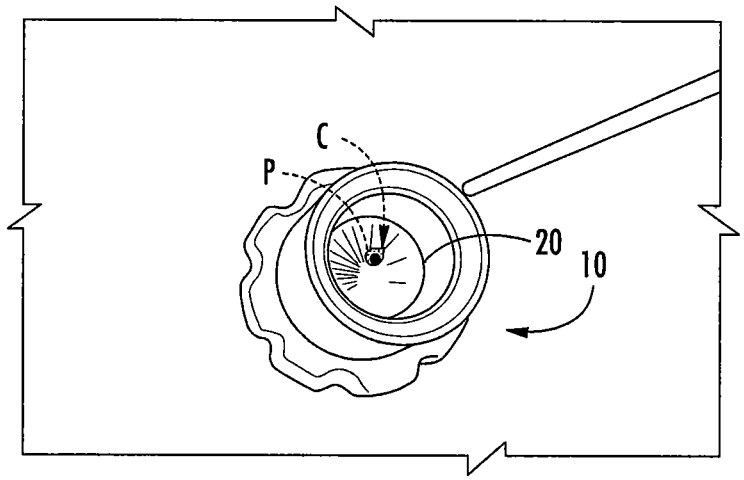
Figure 20:
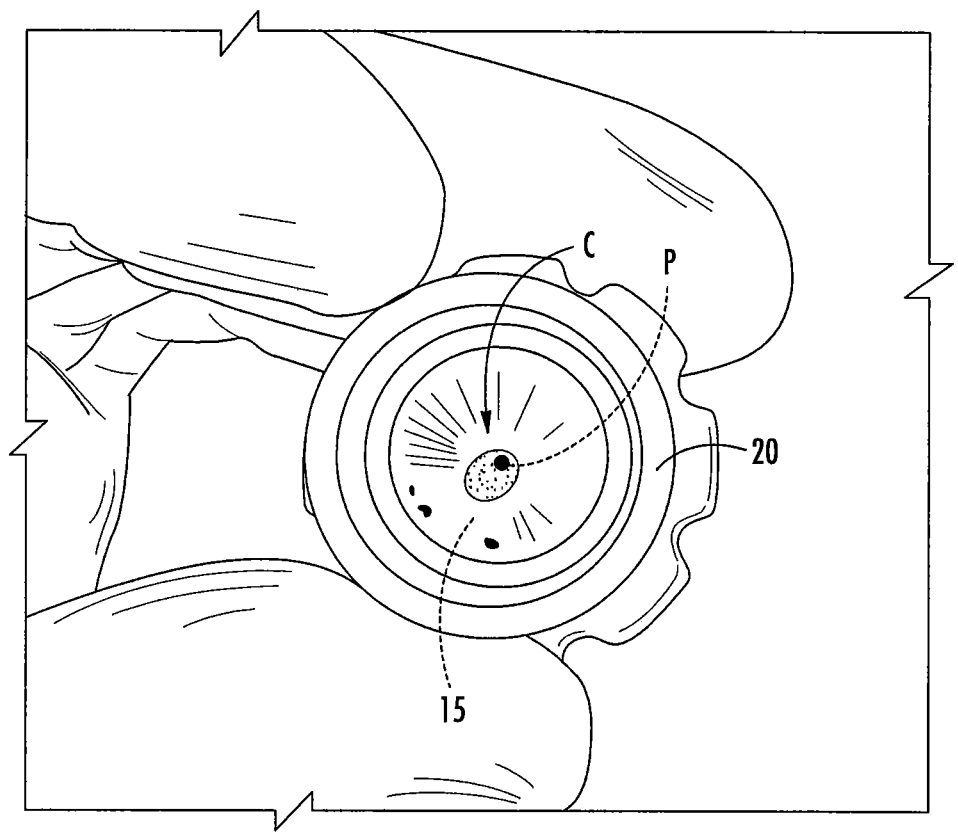

The supernatant (formalin) is aspirated and discarded being careful not to disrupt the pelleted sample P as shown in FIG. 19. FIG. 20 illustrates the tube 10 with a sample pellet P. Some supernatant may remain but does not interfere with subsequent processing.

Figure 21:
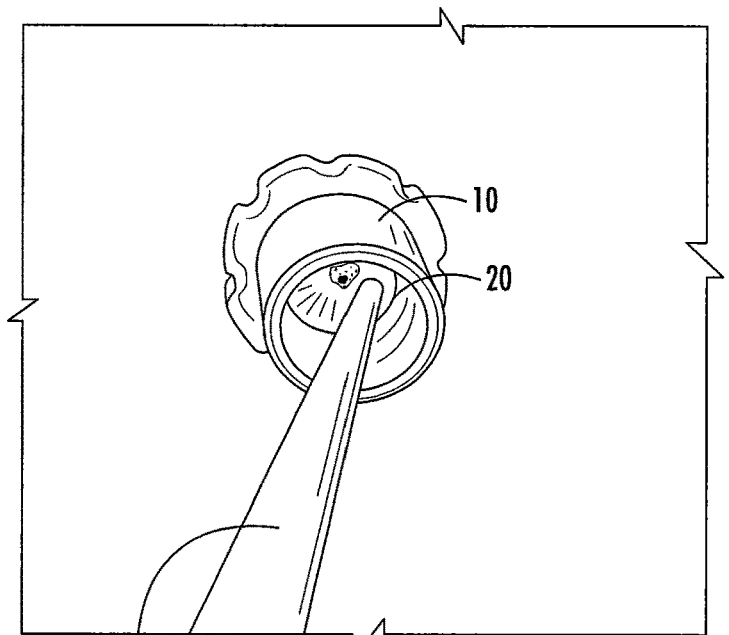
Figure 22:
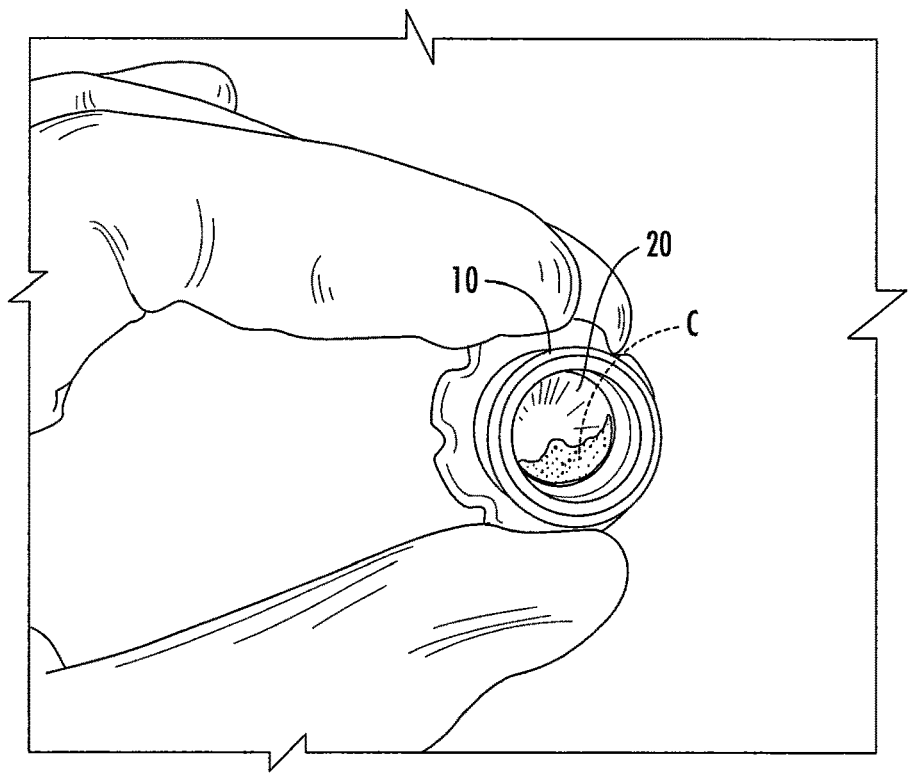
Figure 23:
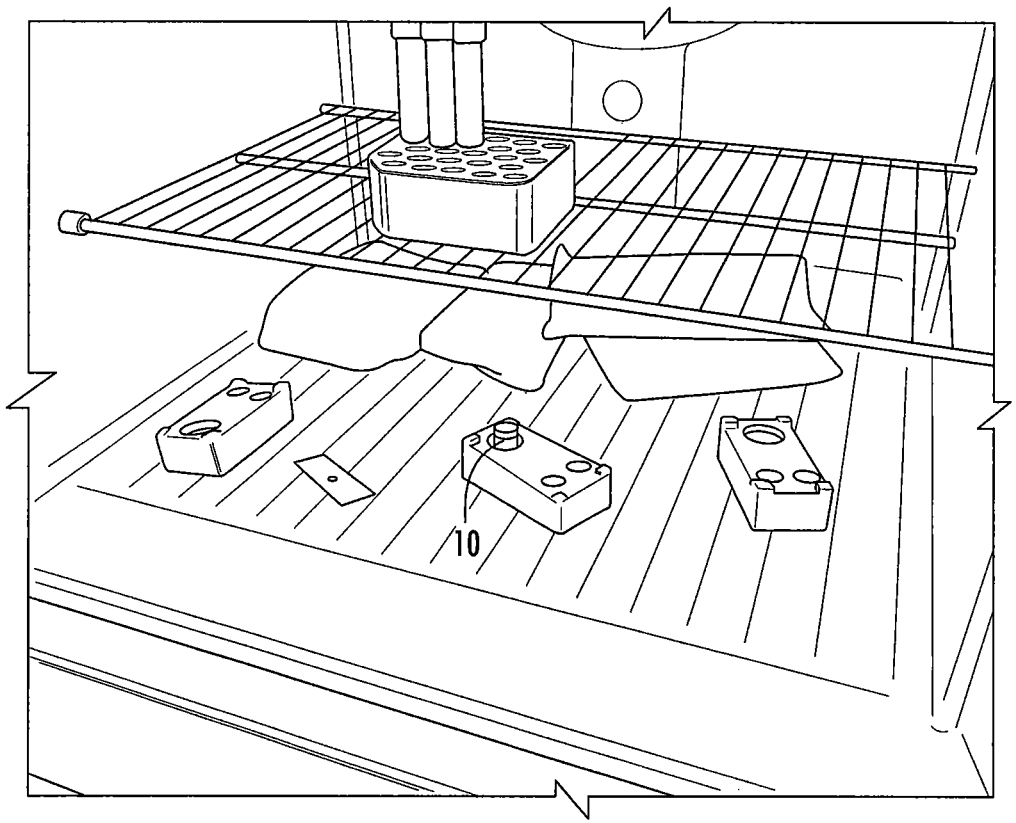

After placing the tube 10 in the tube 50, and centrifuging (as described above), liquid histogel (melted agarose) can be pipetted up and down in the tube 10 as shown in FIG. 21 using pipette 299 to resuspend the sample in the histogel. About 30 μL of agarose may be used for this resuspension although other amounts may also be appropriate. FIG. 22 illustrates that the suspension can be carried out relatively rapidly so that the agarose does not solidify. FIG. 23 shows the tube with the suspended sample in a low temperature freezer (e.g., about −20 C) to facilitate solidification, which can occur in between about 2-5 minutes.

Figure 24:
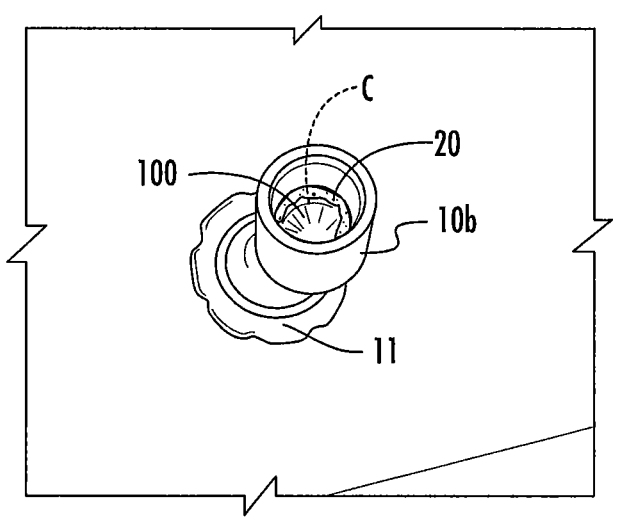
Figure 25:
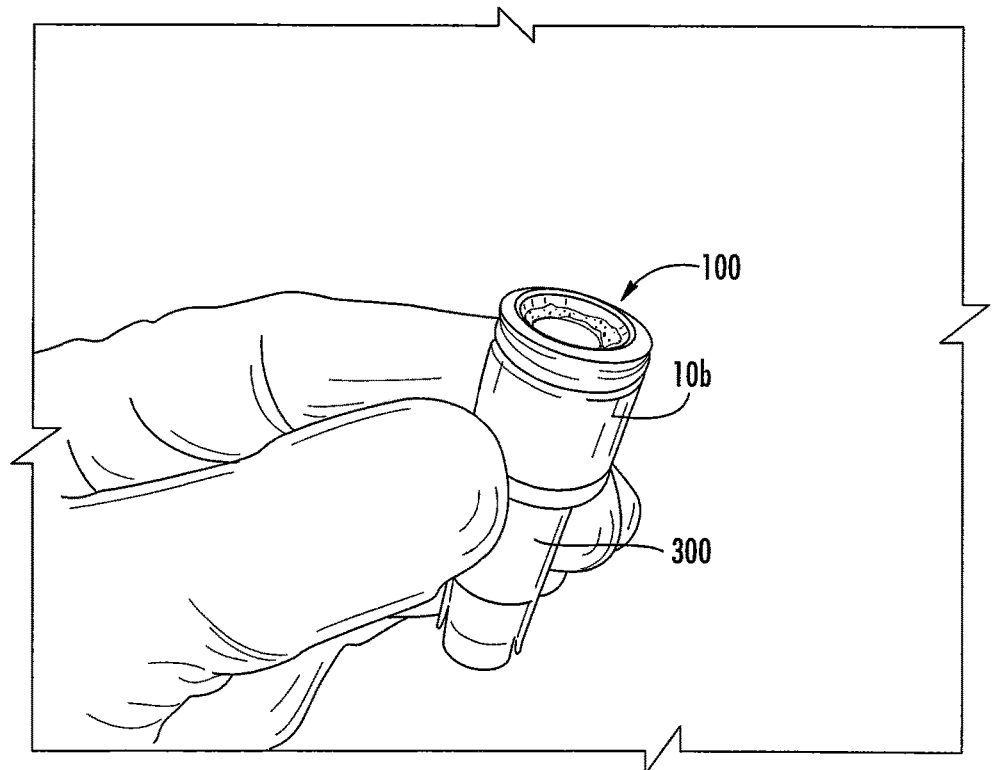

FIG. 24 illustrates the cell block 100 (e.g., the cell bed 20 and the solid histogel with cells) being removed from the tube 10b and/or base 11. FIG. 25 shows that the cell bed 20 may attach to the inner wall of the tube body 10b and may need a plunger or other push member 300 to push the cell bed with the cells, e.g., cell block 100 from the tube body (typically out the top, pushing against the cell bed 20 rather than the cells/histogel (agarose) mixture 100.

Figure 26:
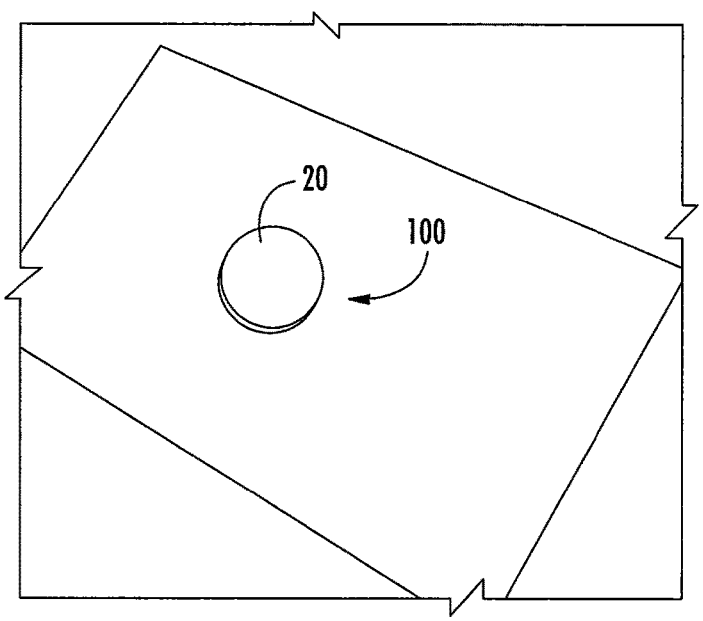
Figure 27:
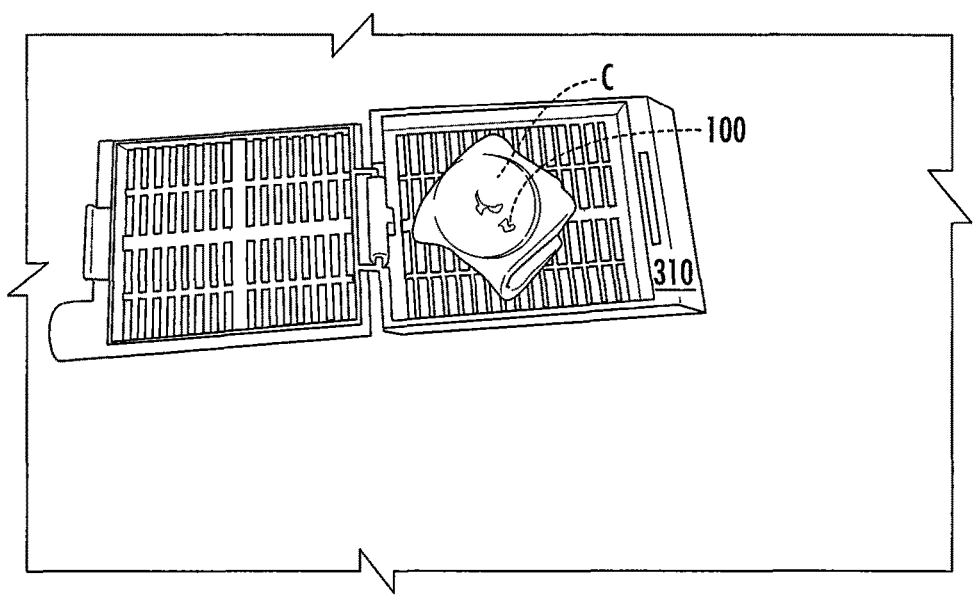

FIG. 26 illustrates the cell block 100 with cell bed 20 placed on routine tissue paper. As is known to those of skill in the art, it is standard practice to wrap the sample 100 in tissue paper in preparation for tissue processing for small histology specimens. FIG. 27 illustrates the tissue paper wrapped cell block 100 with cell bed 20 in a standard histology cassette 310. The darker dots inside the wrapped cell block 100 are cells C.

Although shown as a manual operation, it is contemplated that machines may be used to automatically carry out certain of the above steps.

Table 1 below is a list of 15 cases of data comparing an exemplary collection vessel with the standard methods. All cases were graded from 1 (poor) to 2 (adequate) to 3 (superior). The first row is the diagnosis. The 2nd row is the paired smear quality (DQ and H&E). The CBCS is the remnant material left on the traditional clotting slide. The clot blot is the standard method compared to the cell disk method (CD). Last level was the last recut level on the FFPE block. The method was overall graded for superiority. As seen, the standard method was never superior to the new CD method but equivocal in some cases.

TABLE 1

DATA SUMMARY

| Pathologic Diagnosis | Smear Quality (1-3) | CBCS (1-3) | Clot Blot Quality (1-3) | Cell Disk Quality (1-3) | Last Level | Best Method |
|---|---|---|---|---|---|---|
| Oncocytoma | 2 | 2 | 1 | 2 | 3 | CD |
| RCC, clear cell | 3 | 1 | 1 | 2 | 3 | CD |
| Pleomorphic adenoma | 3 | 2 | 1 | 2 | 3 | CD |
| Large cell carcinoma | 3 | 3 | 3 | 3 | 3 | Tied |
| Adenocarcinoma | 3 | 2 | 3 | 3 | 5 | Tied |
| Scc | 2 | 3 | 2 | 2 | 3 | Tied |
| Urothelial carcinoma | 3 | 2 | 2 | 1 | 3 | CD |
| Invasive ductal carcinoma | 3 | 1 | 3 | 3 | 3 | CD |
| Hodgkin lymphoma | 3 | 3 | 3 | 3 | 9 | CD |
| RCC, papillary | 2 | n/a | 3 | 3 | 3 | CD |
| Follicular adenoma | 3 | 3 | 2 | 2 | 5 | Tied |
| Solid-pseuodopapillary | 3 | 1 | 1 | 1 | 5 | Tied |
| Urothelial carcinoma | 2 | 1 | 1 | 2 | 3 | CD |
| Oncocytoma | 3 | 3 | 3 | 3 | 5 | CD |
| Scc | 3 | 2 | 1 | 2 | 5 | CD |

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of collecting and processing a biosample, comprising:

providing a tubular container with an internal cavity sealably attached to a base providing a cell bed, wherein the cell bed comprises an inert solid cell bed surface that is capable of supporting processed cell material;

inserting a biosample comprising cells into the tubular container so that cells reside on the cell bed;

placing the tubular container with the cell bed and biosample in a centrifuge;

centrifuging the biosample in the tubular container so that cells from the biosample deposit as a pellet against the cell bed;

inserting a liquid matrix material in the tubular container above the cell bed;

forming a solid cell block of the liquid matrix material holding distributed cells therein above the cell bed in the tubular container; and detaching the base from the tubular container to expose the solid cell block on the cell bed provided by the base.

2. The method of claim 1, wherein the cell bed is a solid, shape-changeable, moldable material that is able to change in shape in response to forces above those applied during the centrifuging step and can retain that shape during the inserting, centrifuging, forming and detaching steps.

3. The method of claim 1, wherein the cell bed comprises solid paraffin and extends across the tubular container.

4. The method of claim 1, wherein the cell bed has a middle portion with a substantially conical shape that merges into an outer cylindrical upwardly extending portion.

5. The method of claim 1, wherein the inserting the biosample is carried out by depositing cells from a fine needle aspirate directly from a needle holding the aspirate onto the cell bed.

6. The method of claim 1, wherein the placing the tubular container in the centrifuge is carried out by first placing the tubular container holding the biosample on the cell bed in a coupler, adapter or larger tube forming a centrifuge assembly, then placing the assembly in a bucket of the centrifuge and centrifuging the assembly to centrifuge the biosample.

7. The method of claim 1, wherein the cell block comprises cells from a fine needle aspirate tissue sample.

8. The method of claim 1, further comprising replacing a first cap with a second cap holding an elongate body thereabove with a fluid port in fluid communication with the internal cavity of the tubular container and with the base attached to the tubular container.

9. The method of claim 1, further comprising, before the centrifuging step, inverting the tubular container with the cell bed, then attaching the tubular container to an open end of an elongate body comprising a liquid and having a length greater than the tubular container, then inverting the tubular container with the cell bed while attached to the elongate body with the liquid so that the cell bed is at a lower end of the tubular container, then centrifuging the biosample in the tubular container.

10. The method of claim 1, wherein the base comprises a wall surrounding an annular space, and wherein the wall comprises threads that couple to threads on a bottom end portion of the tubular container.

11. A method of collecting a biosample, comprising:
providing a tubular container with an internal cavity sealably attached to a base, wherein the base comprises an annular space bounded by a wall with threads that couple to threads on a bottom end of the tubular container, wherein the base provides a solid cell bed with an inert solid cell bed surface adjacent the bottom end of the tubular container;

inserting a needle with a fine needle aspirate (FNA) sample comprising cells into the tubular container so that cells reside on the cell bed; and either
(i) placing a cap on the tubular container before or after inserting the biosample or (ii) attaching the tubular container with the base that provides the solid cell bed to an elongate body with liquid and cells from other passes of FNA, wherein the elongate body has a length that is greater than the tubular container.

12. The method of claim 11, wherein the cell bed has a middle portion with a substantially conical shape that merges into an outer cylindrical upwardly extending portion.

13. A method of processing a biosample, comprising:
obtaining a tubular container with an internal cavity having a sealably attached base providing a cell bed with an inert solid cell bed surface and a biosample comprising cells that reside on the inert solid cell bed surface of the cell bed;

centrifuging the biosample in the obtained tubular container with the sealably attached base so that cells from the biosample deposit as a pellet against the cell bed; then inserting a liquid matrix material in the obtained tubular container above the cell bed; then forming a solid cell block of the liquid matrix material holding distributed cells therein above the cell bed in the obtained tubular container with the sealably attached base; and detaching the base from the obtained tubular container to expose the solid cell block held by the base.

14. The method of claim 13, wherein the cell bed is a solid, shape-changeable, moldable material that is able to change in shape in response to forces above those applied during the centrifuging step and can retain that shape during the inserting, centrifuging, forming and detaching steps.

15. The method of claim 13, wherein the cell bed comprises solid paraffin and extends across the tubular container.

16. The method of claim 13, wherein the cell bed has a middle portion with a substantially conical shape that merges into an outer cylindrical upwardly extending outer portion.

17. The method of claim 13, wherein, before the centrifuging, the method includes placing the obtained tubular container with the sealably attached base holding the biosample on the cell bed in a coupler, adapter or larger tube forming a centrifuge assembly, then placing the assembly in a bucket of the centrifuge and centrifuging the assembly for the centrifuging of the biosample in the obtained tubular container.

18. The method of claim 13 wherein the tubular container with the sealably attached base holding the biosample is also attached to an elongate body on an end opposing the base, wherein the elongate body has a length that is greater than the tubular container, wherein the elongate body comprises liquid with supplemental cells from needles used to obtain additional fine needle aspirates of target tissue corresponding to the biosample on the cell bed, and wherein the centrifuging is carried out to form a pellet of the biosample cells and the supplemental cells.

19. The method of claim 13, wherein the cell block comprises cells from a fine needle aspirate tissue sample.

20. The method of claim 13, wherein the base comprises a wall surrounding an annular space, and wherein the wall comprises threads that sealably attach to threads on a bottom end portion of the tubular container to form a fluid tight seal.

* * * * *